United States Patent [19]

Kawamura et al.

[11] 4,315,983
[45] Feb. 16, 1982

[54] 2,6-DI-TERT-BUTYL-4-SUBSTITUTED THIOPYRYLIUM SALT, PROCESS FOR PRODUCTION OF SAME, AND A PHOTOCONDUCTIVE COMPOSITION CONTAINING SAME

[75] Inventors: Koichi Kawamura; Harumi Katsuyama; Hideo Sato, all of Asaka, Japan

[73] Assignee: Fuji Photo Film Co., Ltd., Kanagawa, Japan

[21] Appl. No.: 168,855

[22] Filed: Jul. 14, 1980

[30] Foreign Application Priority Data

| Jul. 13, 1979 | [JP] | Japan | 54-88317 |
| Jul. 13, 1979 | [JP] | Japan | 54-88318 |
| Aug. 21, 1979 | [JP] | Japan | 54-105546 |
| Aug. 21, 1979 | [JP] | Japan | 54-105547 |
| Aug. 31, 1979 | [JP] | Japan | 54-110457 |

[51] Int. Cl.³ .............................................. G03G 5/09
[52] U.S. Cl. ........................................ 430/70; 430/83; 430/81; 430/95; 430/82; 542/448; 542/449; 542/471; 542/473; 542/454; 549/13
[58] Field of Search ................ 542/448, 549, 471, 473, 542/454; 549/13; 430/81, 83, 82, 95

[56] References Cited

U.S. PATENT DOCUMENTS 4,283,475  8/1981  Kawamura et al. ................ 430/81

*Primary Examiner*—John D. Welsh
*Attorney, Agent, or Firm*—Sughrue, Mion, Zinn, Macpeak and Seas

[57] ABSTRACT

2,6-Di-tert-Butyl-4-substituted thiopyrylium salt represented by formula (I), a process for production of said salt and a photoconductive composition containing said salt.

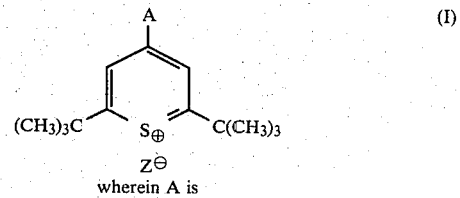

wherein A is

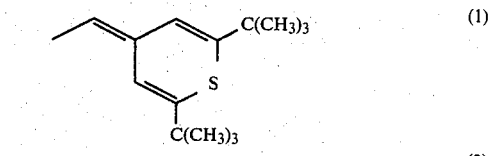

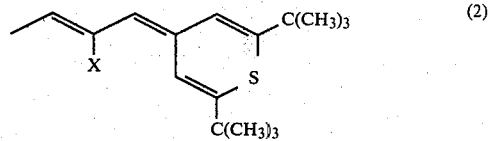

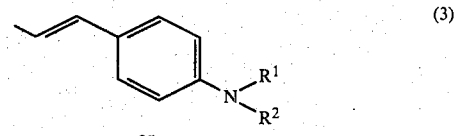

or

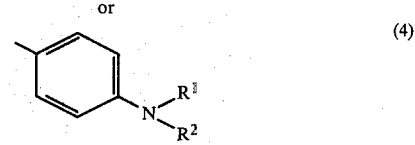

wherein $Z^{\ominus}$ is an anion, X is a hydrogen atom, an aryl group, a substituted aryl group or an alkyl group, and $R^1$ and $R^2$ are the same or different and include alkyl groups.

47 Claims, 9 Drawing Figures

2,6-DI-TERT-BUTYL-4-SUBSTITUTED THIOPYRYLIUM SALT, PROCESS FOR PRODUCTION OF SAME, AND A PHOTOCONDUCTIVE COMPOSITION CONTAINING SAME

BACKGROUND OF THE INVENTION

1. Field of the Invention

This invention relates to a 2,6-di-tert-butyl-4-substituted thiopyrylium salt, a process for the production of said salt and a photoconductive composition containing said salt.

2. Description of the Prior Art

As is known in the art, thiopyrylium and pyrylium dyes are used in various applications. For example, as disclosed in Japanese Patent Publication No. 40900/71, they are used in a direct positive photographic silver halide emulsion as an electron acceptor. They are also useful as a spectral sensitizer for a photoconductor, especially an organic photoconductor, as taught in Davis et al, U.S. Pat. No. 3,141,700, Van Allan et al, U.S. Pat. No. 3,250,615 and Reynolds et al, U.S. Pat. No. 3,938,994.

Photoconductors sensitized with thiopyrylium and pyrylium dyes are used in the various applications as disclosed in the above-described patents, and they are particularly important for use in electrophotography such as xerography or electrofax.

Hitherto known thiopyrylium dyes, however, suffer from the disadvantage that they have a plurality of absorption bands in the visible region. In particular, almost all of the dyes exhibit absorption in the blue region. This means that the dyes spectral sensitize in a plurality of wave length regions. Therefore, in forming a color image by use of such thiopyrylium dyes as a sensitizer for photoconductive particles, for example, in obtaining a color image from a mixture of three colored particles according to the photoelectrophoretic electrophotography, serious problems occur.

The principle of the photoelectrophoretic electrophotography is detailed in U.S. Pat. No. 3,384,448, according to which a suspension of photoconductive photosensitive particles in an insulating liquid is placed between a pair of electrodes, at least one of which is transparent to light and across which a differential voltage is applied and the suspension is exposed imagewise through the transparent electrode. The photoconductive photosensitive particles selectively migrate to one electrode to form a visible image on that electrode.

To produce a polychromatic image, a suspension comprising a mixture of cyan colored particles sensitive to red light, magenta colored particles sensitive to green light and yellow colored particles sensitive to blue light is set on the above described system wherein it is exposed imagewise through a multicolor original image, e.g., a color slide (or by the reflective printing method) using white light, and one operation of imagewise exposure produces a subtractive color positive or negative image on the transparent electrode.

Illustrative particles suitable for producing such subtractive color images are described in U.S. Pat. No. 3,384,448, Japanese Patent Publication No. 21781/68 (U.S. Pat. Nos. 3,681,064 and 3,384,556) and Japanese Patent Application (OPI) No. 143822/77 (U.S. Pat. No. 4,032,339) (the term "OPI" as used herein refers to a "published unexamined Japanese patent application"), and they are cyan, magenta and yellow pigments the principal absorption bands of which correspond to their principal sensitive regions.

In addition to these three colored photoconductive pigments, U.S. Pat. No. 3,384,448 teaches electrically photosensitive particles which contain a spectral sensitizer so that they are sensitive to radiation in the visible spectral range.

In obtaining a color image from such a mixture of three colored particles according to the photoelectrophoretic electrophotographic method, the use of known thiopyrylium dyes as a spectral sensitizer for photosensitive particles has resulted in the formation of those images having insufficient color separation because of their spectral sensitization in a plurality of wave length regions.

This indicates that the known thiopyrylium dyes have been unsuitable for use in the production of color images by the photoelectrophoretic electrophotographic method.

The inventors have found novel thiopyrylium dyes which are free from the disadvantages as described above and provide photoconductive substances with higher sensitivity than do conventional thiopyrylium dyes, and a process for the production of said thiopyrylium dyes.

SUMMARY OF THE INVENTION

An object of this invention is to provide a thiopyrylium salt which provides a photoconductive substance with high sensitivity, a process for the production of said thiopyrylium salt, and a photoconductive composition comprising a photoconductive substance containing said thiopyrylium salt as a sensitizer.

Another object of this invention is to provide a thiopyrylium salt for use in the formation of an image having excellent color separation, a process for the production of said thiopyrylium salt, and a photoconductive composition comprising a photoconductive substance containing said thiopyrylium salt as a sensitizer.

DETAILED DESCRIPTION OF THE INVENTION

Figure 1:
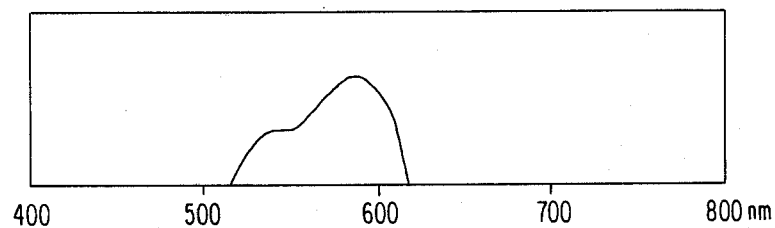
FIGS. 1 to 4 are spectral sensitivity spectra of photoconductive compositions comprising poly(n-vinyl carbazole) containing the thiopyrylium dyes of this invention.
Figure 2:
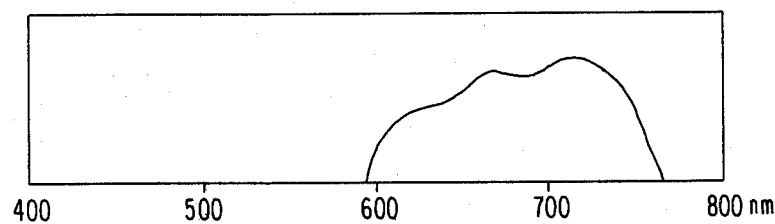
Figure 3:
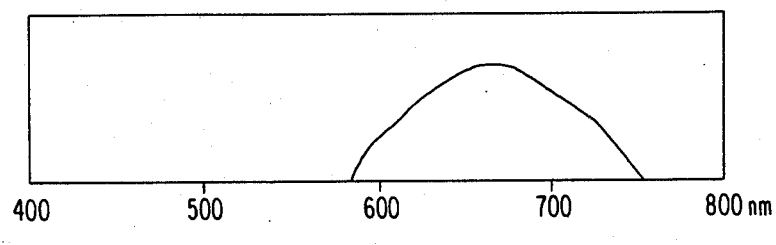
Figure 4:
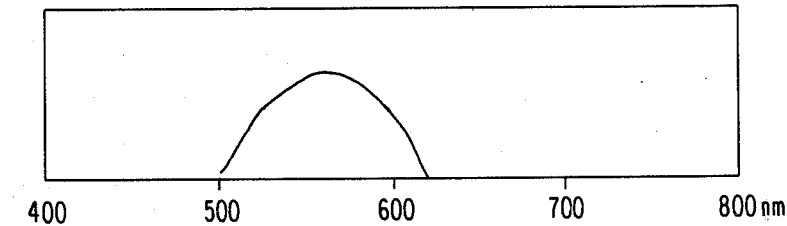
Figure 5:
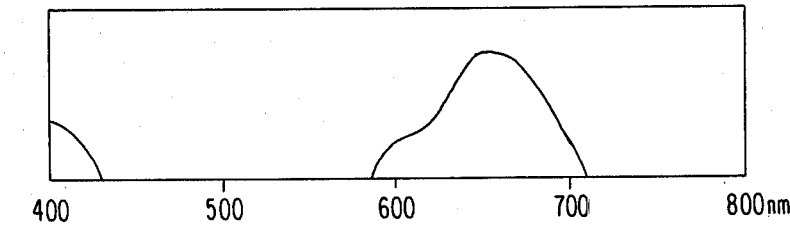
FIGS. 5, 6, 7 and 8 are spectral sensitivity spectra of photoconductive compositions containing conventional thiopyrylium dyes.
Figure 6:
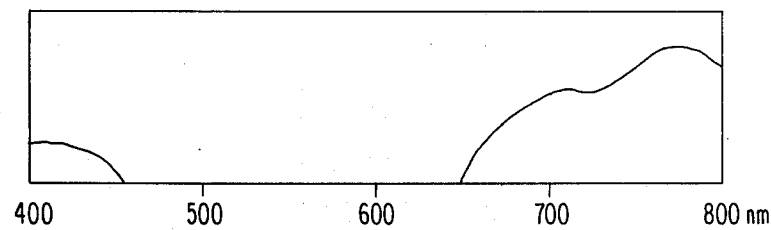
Figure 7:
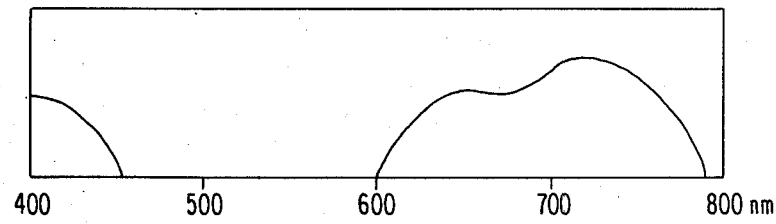
Figure 8:
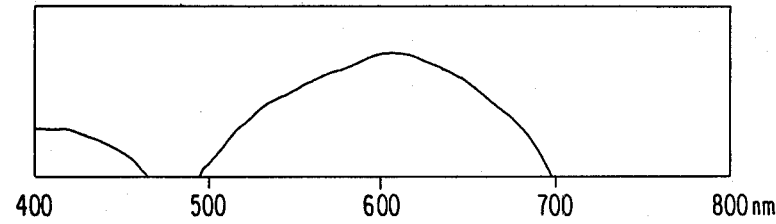

The thiopyrylium salts of this invention are the thiopyrylium dyes represented by the formula as shown below, and they are used as a sensitizer for photoconductive substances.

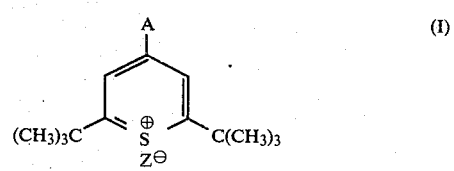

(I)

wherein A represents

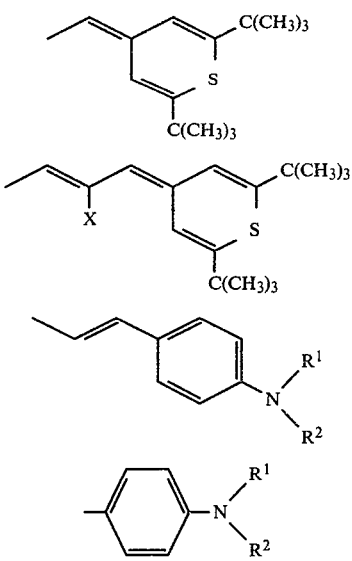

and $Z^\ominus$ represents an anion. In group A, X represents a hydrogen atom, an aryl group, a substituted aryl group or an alkyl group, wherein the substituent in the substituted aryl group includes a halogen atom, a nitro group, an alkoxy group, or an alkyl group. X preferably represents a hydrogen atom, an alkyl group having 1 to 4 carbon atoms, a phenyl group, a p-bromophenyl group, a p-methoxyphenyl group or a p-tolyl group; $R^1$ and $R^2$ are the same or different and include alkyl groups, preferably having 1 to 4 carbon atoms.

In more detail, the thiopyrylium salts of this invention are Compounds (a), (b), (c) and (d) as shown below, wherein X, $R^1$ and $R^2$ have the same significance as above:

(a) 2,6-di-tert-Butyl-4-(2,6-di-tert-butyl-4H thiopyran-4-ylidenemethyl)thiopyrylium Salt.

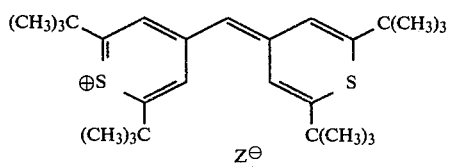
I-(1)

(b) 2,6-di-tert-Butyl-4-[3-(2,6-di-tert-butyl-4H-thiopyran-4-ylidene)propene-1-yl]thiopyrylium Salt or derivatives thereof.

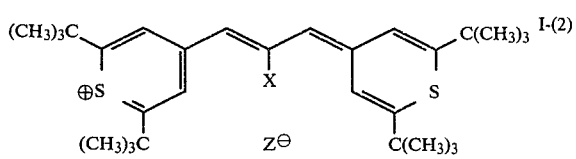
I-(2)

Illustrative examples of Salt I-(2) are a 2,6-di-tert-butyl-4-[3-(2,6-di-tert-butyl-4H-thiopyran-4-ylidene)-propene-1-yl]thiopyrylium salt of the formula:

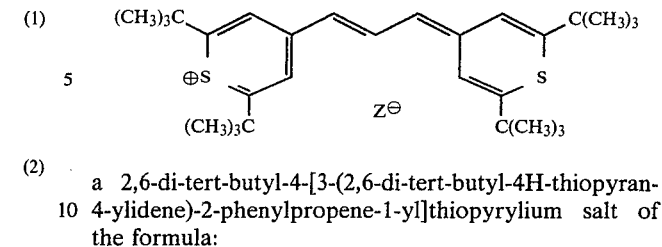

a 2,6-di-tert-butyl-4-[3-(2,6-di-tert-butyl-4H-thiopyran-4-ylidene)-2-phenylpropene-1-yl]thiopyrylium salt of the formula:

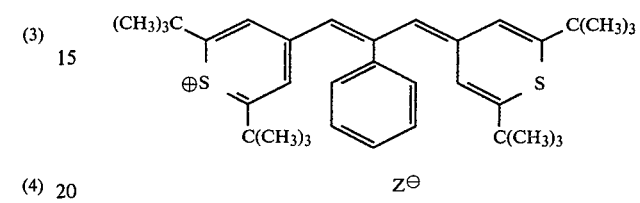

and a 2,6-di-tert-butyl-4-[3-(2,6-di-tert-butyl-4H-thiopyran-4-ylidene)-2-(4-bromophenyl)propene-1-yl]thiopyrylium salt of the formula:

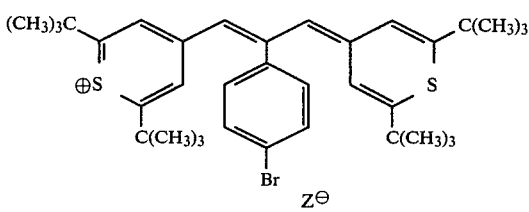

(c) 2,6-di-tert-Butyl-4-(4-disubstituted aminostyryl)-thiopyrylium Salt

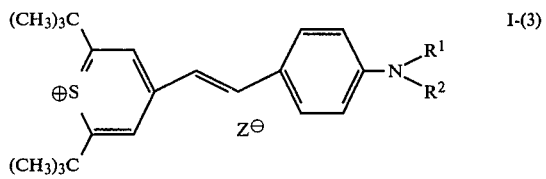
I-(3)

Illustrative examples of salt I-(3) are a 2,6-di-tert-butyl-4-(4-diethylaminostyryl)thiopyrylium salt of the formula:

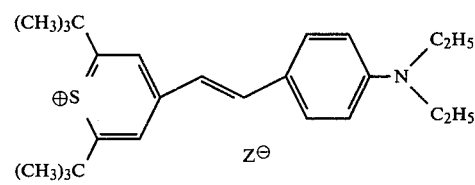

and a 2,6-di-tert-butyl-4-(4-dimethylaminostyryl)thiopyrylium salt of the formula:

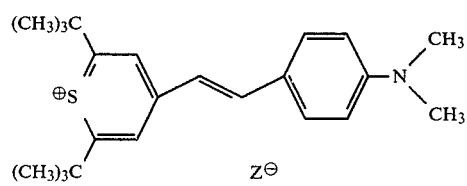

(d) 2,6-di-tert-Butyl-4-(4-disubstituted aminophenyl)-thiopyrylium Salt

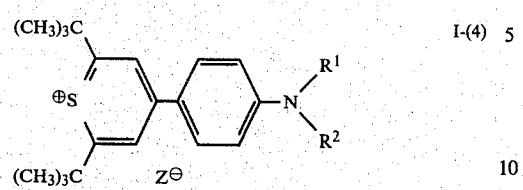

Illustrative examples of salt I-(4) are a 2,6-di-tert-butyl-4-(4-diethylaminophenyl)thiopyrylium salt of the formula:

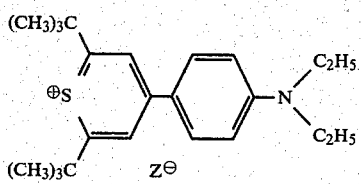

a 2,6-di-tert-butyl-4-(4-dimethylaminophenyl)thiopyrylium salt of the formula:

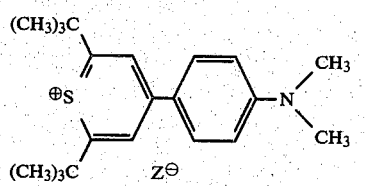

a 2,6-di-tert-butyl-4-(4-dipropylaminophenyl)thiopyrylium salt, etc.

In the above formulae, $Z^{\ominus}$ represents an anion, i.e., well known negatively charged atoms or groups of atoms, and it is preferably an anionic functional group wherein the acid represented by HZ is a strong acid having a pKa of 5 or less, preferably a pKa of 2 or less.

Illustrative examples of the negatively charged atom as the anionic function include halides such as fluoride, chloride, bromide and iodide ions.

Illustrative examples of the negatively charged group of atoms as the anionic function include organic anions such as trifluoroacetate, trichloroacetate and p-toluenesulfonate ions and inorganic anions such as perchlorate, periodate, tetrachloroaluminate, trichloroferrate (II), tetrafluoroborate, hexafluorophosphate, sulfate, hydrogensulfate and nitrate ions. For the purpose of this invention, these anionic functions include divalent anions such that half of a divalent anionic function represents a monovalent anionic function. Of these anions, chloride, bromide, perchlorate, tetrafluoroborate, p-toluenesulfonate and trifluoroacetate ions are preferred.

The thiopyrylium salt of formula I-(1) can easily be obtained by reacting a 2,6-di-tert-butyl-4-methylthiopyrylium salt represented by the formula (i) illustrated below and a 2,6-di-tert-butyl-4-(alkylthio) thiopyrylium salt represented by the formula (ii) illustrated below in a solvent (Method (i)-[I-(1)]).

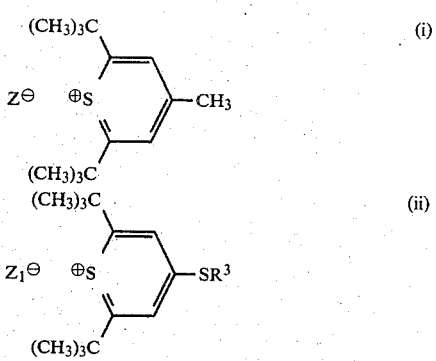

In formula (ii), $R^3$ is an alkyl group containing 1 to 6 carbon atoms, e.g., methyl and ethyl, or a substituted alkyl group, wherein the alkyl group contains 1 to 6 carbon atoms. Suitable substituents for the substituted alkyls include phenyl, nitro- or halogen-substituted phenyl, alkoxy containing 1 to 5 carbon atoms, amino and sulfonic acid groups. Of these substituents, methyl, ethyl and benzyl groups are preferred.

$Z^{\ominus}$ represents the same anion described above. $Z_1^{\ominus}$ is the residue of an alkylating agent which is used in the synthesis of Compound of formula (ii). Halogen anions, e.g., iodide, bromide, chloride and fluoride, methylsulfate, fluorosulfate and tetrafluoroborate are preferred.

Various organic solvents can be used as the solvent, and those solvents in which Compounds of formulae (i) and (ii) are readily soluble are preferably used. Representative examples are nitriles such as acetonitrile and propionitrile, ketones such as acetone and methyl ethyl ketone, organic carboxylic acids such as acetic acid, alcohols such as benzyl alcohol and acid anhydrides such as acetic anhydride.

Compound of formula (ii) is added in an amount of about 0.5 to 5 moles per mole of Compound of formula (i), with the range of 0.8 to 1.5 moles being preferred. From the solubilities of Compounds of formulae (i) and (ii), and the economic standpoint, the solvent is used in an amount of about 0.5 to 100 ml per gram of the total amount of Compounds of formulae (i) and (ii), preferably about 1 to 50 ml, and more preferably about 3 to 10 ml.

The reaction temperature is from 25° C. to 200° C., preferably from 60° C. to the reflux temperature of the solvent, i.e., 140° C. The reaction time is from 10 minutes to 10 hours, preferably from 10 minutes to 2 hours. Where acetic anhydride is used as the solvent, the maximum yield is obtained at a reaction temperature of about 100° C. and a reaction time of 30 minutes.

To accelerate the reaction of Compounds of formulae (i) and (ii), a base can be added to the reaction system. Suitable bases are, for example, trialkyl amines such as triethylamine, aromatic amines such as pyridine, and salts such as sodium acetate, sodium carbonate and potassium carbonate. While these bases are optional, they yield good results. Alternatively, bases such as pyridine can be used as the solvent. The amount of base being added is about 0.01 to 20 moles per mole of Compound of formula (i), preferably 0.1 to 5 moles.

The thiopyrylium salt of formula (ii) for use in the above reaction is a novel compound and can be synthesized from 2,6-di-tert-butyl-4H-pyran-4-one, which has been synthesized as described in G. A. Reynolds et al, Journal of Heterocyclic Chemistry, Vol. 11, page 1075 (1974), in the following three steps.

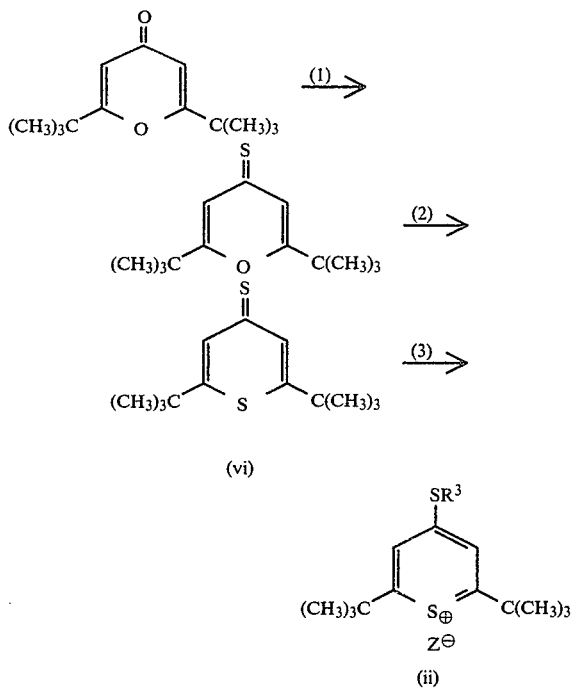

(vi)

The starting material, 2,6-di-tert-butyl-4H-pyran-4-one is heated in the presence of phosphorus pentasulfide at Step (1) according to the process described in the above *Journal of Heterocyclic Chemistry* (page 1075). The reaction product of 2,6-di-tert-butyl-4H-pyran-4-thione is then reacted with alkali sulfide such as sodium sulfide or alkali hydrosulfide such as potassium hydrosulfide in a solvent at a temperature between 50° C. to 200° C. in an atmosphere of an inert and oxygen-free gas such as $N_2$, $CO_2$, and argon gas (Step 2) to produce compound of formula (vi) (2,6-di-tert-butyl-4H-thiopyran-4-thione). The solvent used at Step 2 is water-free and non aqueous solvent having at least 20 of dielectric constant and at least 2 of dipole moment, for example, hexamethyl phosphoric triamide, dimethylsulfoxide, N,N-dimethylformamide or N-methylpyrrolidone. The alkali sulfide or alkali hydrosulfide used is 1 to 30 moles, preferably 3 to 20 moles, per 1 mole of 2,6-di-tert-butyl-4H-pyran-4-thione. Compound of formula (vi) is then reacted with an alkylating agent at Step (3) to obtain the thiopyrylium salt of formula (ii). The reaction temperature at Step 3 is −10° C. to 200° C., preferably 40° C. to 100° C. and the reaction time is 30 minutes to 2 hours. In formula (ii), $R^3$ is an alkyl or substituted alkyl group derived from the alkylating agent.

Examples of such alkylating agents are methyl halide such as methyl iodide, methyl bromide, methyl chloride and methyl fluoride, methylating agents such as trimethyloxonium tetraborate, dimethylsulfuric acid and methylfluorosulfate, ethyl halide such as ethyl iodide and ethyl bromide, ethylating agents such as ethyl-p-toluene sulfonate, diethylsulfuric acid and triethyloxonium tetrafluoroborate, benzyl halide such as benzyl chloride, benzyl bromide and benzyl iodide, benzylating agents such as benzyl-p-toluene sulfonate, and usually known alkylating agents. The amount of an alkylating agent is 1 to 50 moles per 1 mol of 2,6-di-tert-butyl-4H-thiopyran-4-thione, preferably 1 to 20 moles. Solvent, for example, ketone such as acetone, methylethyl-ketone, acetonitrile, and halogenized hydrocarbon such as chloroform may be used and the alkylating agent is also used as a solvent.

Each step is preferably carried out by a batch method rather than a continuous method.

The thiopyrylium salt of formula (i), the other starting material, is a novel compound, and it can be synthesized by reacting 2,6-di-tert-butyl-4H-thiopyran-4-one (compound of formula (iii), which is obtained by hydrolysis of the 2,6-di-tert-butyl-4-(alkylthio)thipyrylium salt of formula (i) or a 2,6-di-tert-butyl-4-(arylthio)thiopyrylium salt or the 2,6-di-tert-butyl-4H-thiopyran-4-thione (Compound (vi)), with a Grignard reagent at a temperature of −20° C. to 25° C. for about 30 minutes to 90 minutes in a solvent and in a non-oxidizing atmosphere and then processing with an acid.

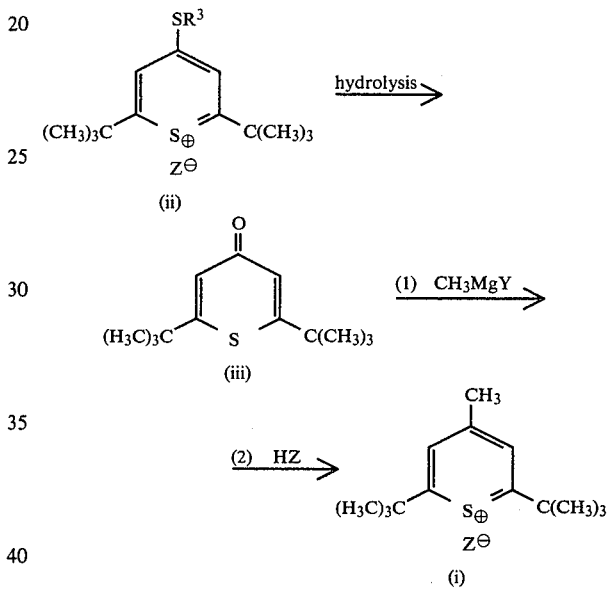

Y is I, Br or Cl; HZ is an acid capable of forming an anion functional group by dissociation; and $Z^\ominus$ is an anion functional group.

For the formation of Compound of formula (iii) used as a starting material in the above reaction scheme, the hydrolysis of Compound of formula (ii) is advantageous over that of Compound of formula (vi) since it leads to the formation of Compound of formula (iii) in high yields.

The hydrolysis is carried out for 10 minutes to 10 hours in water or in a solvent which is miscible with water and having high polarity at least 20 of dielectric constant and at least 1 of dipole moment, such as water, an alcohol, e.g., methanol, ethanol, an ether, e.g.,1,4-dioxane, an amido, e.g., hexamethyl phosphoric triamide, acetoniride, dimethylsulfoxide, sulfolane, etc. The hydrolysis temperature is preferably 80° C. to 100° C. A catalyst for hydrolysis may be used such as acidic catalyst having not more than 5 of pKa value, for example, hydrochloric acid, trifluoroacetic acid, etc., and basic catalyst having at least 9 of pKa value, for example, ammonia, sodium hydroxide, etc.

Preferred Grignard reagents are methylmagnesium iodide, methylmagnesium bromide and methylmagnesium chloride. In place of these Grignard reagents, other organometallic compounds such as methylpotassium, methylsodium, methyllithium, methylcalciumiodide, dimethylberyllium, trimethylaluminum and trimethylboron can be used. The organometallic compound is used in an amount between 1 mol and about 10 moles, preferably 1 to 3 moles per mol of compound of formula (iii).

Non-aqueous solvents containing substantially no water can also be used as the solvent. Examples of such non-aqueous solvents are ether compounds such as dimethyl ether, methyl ethyl ether, diethyl ether, dimethoxyethane, tetrahydrofuran and 1,4-dioxane, aromatic compounds such as benzene and toluene, and saturated hydrocarbon compounds such as pentane, hexane, cyclohexane, methylcyclohexane and petroleum ether.

Preferred acids for use in the above reaction include hydrofluoric acid, hydroiodic acid, hydrochloric acid, hydrobromic acid, perchloric acid, tetrafluoroboric acid, hexafluorophosphoric acid, sulfuric acid, nitric acid, trichloroacetic acid, trifluoroacetic acid and p-toluenesulfonic acid.

By the term "non-oxidizng atmosphere" is meant rare gases typified by helium and argon and inert gases typified by nitrogen. These gases replace air to form a substantially oxygen-free condition under which the reaction is carried out. The pressure of the rare gas or inert gas may be in the neighborhood of atmospheric pressure, but this is just one example of the reaction pressure and suitable values may be selected depending on the case.

The synthesis of these starting materials of the formulae (i) and (ii) are described in Japanese Patent Application No. 37249/79 filed on Mar. 28, 1979 and Japanese Patent Application Nos. 81523/79, 81524/79 and 81525/79 filed on June 29, 1979.

The thus obtained compound of the formula (I-(1)) can be purified by a conventional method; the crystals are filtered and recrystallized from a solvent such as ethyl acetate and alcohol, e.g., methanol, esopropanol.

In addition to Method (i)-[I-(1)], the following methods can be employed for the production of Compound I-(1):

Method (ii)-[I-(1)] wherein the 2,6-di-tert-butyl-4-methylthiopyrylium salt as used in Method (i)-[I-(1)] is reacted with an equivalent mole of 2,6-di-tert-butyl-4H-thiopyran-4-one in acetic anhydride in the amount of 5 to 50 ml per gram of the 2,6-di-tert-butyl-4-methylthiopyrylium salt at the reflux temperature thereof for 10 minutes to 5 hours, preferably from 10 to 2 hours;

Method (iii)-[I-(1)] wherein the 2,6-di-tert-butyl-4-methylthiopyrlium salt is reacted with an orthonitroaryl compound such as 1-fluoro-2,4-dinitrobenzene in a solvent;

Method (iv)-[I-(1)] wherein the 2,6-di-tert-butyl-4-methylthiopyrylium salt is reacted with a 2,6-di-tert-butylthiopyrylium salt in a solvent;

Method (v)-[I-(1)] wherein the 2,6-di-tert-butylthiopyrylium salt is reacted with malonic acid in the presence or absence of a base such as sodium acetate; and Method (vi)-[I-(1)] wherein the 2,6-di-tert-butyl-4-methoxythiopyrylium salt if reacted with malonic acid in the presence of trialkylamine or the like.

Of these methods, Method (i)-[I-(1)] is the most preferred for the reson that Compound of formula (ii), one of the starting materials, can be obtained at an early stage of the synthesis and that the yield is higher than those of the other methods.

According to U.S. Pat. No. 3,938,994 as described hereinbefore, conventional thiopyrylium dyes are produced by reacting a pyranomethylenepyrylium salt and sodium sulfide. It is to be noted that this method cannot be used for the synthesis of the thiopyrylium dyes of this invention since only one pyran ring of the pyranomethylenepyrylium salt is converted into a thiopyran ring, that is, two oxygen atoms in pyran rings are not replaced with sulfur atoms at the same time.

The thiopyrylium salt of this invention which is represented by Formula I-(2) can easily be synthesized by reacting a 2,6-di-tert-butyl-4-methylthiopyrylium salt of Formula (i) as illustrated below and diphenylformamidine, the hydrochloride thereof, benzoyl chloride, p-substituted-benzoyl chloride, and alkyl-N,N-diphenyl formamidine, the alkyl group having 1 to 4 carbon atoms, such as N,N-diphenylacetamidine, and N,N-diphenyl propionamidine (Method i-[I-(2)]). In the p-substituted-benzoyl chloride, the substituent is a halogen atom such as Br, a nitro group, an alkoxy group such as methoxy group, or an alkyl group such as methyl group. Preferable p-substituted benzoyl chloride is a p-bromobenzoyl chloride, a p-nitrobenzoyl chloride, a p-methoxybenzoylchloride or a p-methylbenzoyl chloride.

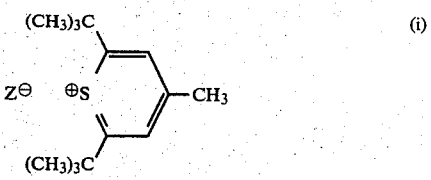

wherein $Z^\ominus$ represents an anion.

The amount of the diphenylformamidine or the hydrochloride thereof being used is from about 0.2 to 5 moles per mole of Compound of formula (i), preferably from 0.3 to 1 mole.

The reaction of the compound of formula (i) and diphenylformamidine, hydrochloride thereof, benzoyl chloride, p-substituted-benzoyl chloride or alkyl-N,N-diphenyl formamidine can be carried out by any one of the following methods:

Method (A) wherein the reaction is carried out in the presence of an amine; that is, the reaction of Compound (i) and diphenylformamidine, hydrochloride thereof, benzoyl chloride, p-substituted benzoyl chloride or alkyl-N,N-diphenyl formamidine is carried out in the present of amines, e.g., piperidine, alkylamines such as triethylamine, aromatic amines such as aniline and dimethylaniline, and nitrogen-containing unsaturated heterocyclic compounds such as pyridine and quinoline.

The amount of the amine added is about 0.1 to 10 moles per mole of the thiopyrylium salt, preferably 0.5 to 2 moles. In some cases, an excess of the amine if used as the solvent. Other various solvents can be used as the solvent, including alcohols such as ethanol, nitriles such as acetonitrile, ketones such as methyl ethyl ketone, nitro compounds such as nitrobenzene, and halogenated hydrocarbons such as tetrachloroethane. Of these compounds, alcohols such as ethanol are preferred.

The reaction time is from 10 minutes to 10 hours, preferably from 30 minutes to 3 hours. The reaction temperature is from the vicinity of 50° C. to the reflux temperature of the solvent or amine, the temperature in the vicinity of the reflux temperature being preferred.

The amount of the solvent is about 1 to 100 ml per gram of Compound (i), preferably 3 to 10 ml.

Method (B) wherein the reaction is carried out in anhydrous carboxylic acid; that is, the reaction of Compound (i) and diphenylformamidine, hydrochloride thereof, benzoyl chloride, p-substituted benzoyl chloride or alkyl-N,N-diphenylformamidine can be carried out in carboxylic anhydride, for example, acetic anhydride.

The amount of the carboxylic anhydride is 1 to 20 ml per gram of Compound of formula (i), preferably 2 to 10 ml. The reaction time is from 1 minute to 1 hour, preferably from 3 minutes to 10 minutes. The reaction temperature is from the vicinity of 80° C. to the reflux temperature (140° C.), preferably in the vicinity of 100° C.

In Method (B), it is preferred to add potassium acetate or sodium acetate. The amount of the potassium acetate or sodium acetate added is 0.5 to 10 moles per mole of Compound (i), preferably in the vicinity of 1 mole.

In the case of the reaction of Compound of formula (i) and diphenylamidine, Methods (A) and (B) are used. On the other hand, where the hydrochloride of diphenylformamidine is employed, there can be used a method in which the diphenylformamidine hydrochloride and Compound of formula (i) are melt-reacted, as well as Methods (A) and (B). In the case of the diphenylformamidine hydrochloride, this melt-reaction method is preferred.

The thiopyrylium salt of Formula I-(2) can be produced by reacting the 2,6-di-tert-butyl-4-methylthiopyrylium salt of Formula (i) and an orthoformic ester represented by the formula as illustrated below or orthoacetic, orthopropionic, orthobutyric or orthovaleric ester, e.g., methyl, ethyl or n-propyl ester (Method ii-I-(2).

$$HC(OR^4)_3$$

wherein $R^4$ is an alkyl group containing 1 to 5 carbon atoms, such as methyl, ethyl and propyl. Examples of the orthoformic esters are methyl orthoformate, ethyl orthoformate and p-propyl orthoformate.

Solvents for use in the reaction of Compound of formula (i) and the orthocarboxylic esters include carboxylic acids such as acetic anhydride and acetic acid, amines such as pyridine and piperidine, nitriles such as acetonitrile, ketones such as methyl ethyl ketone, nitrocompounds such as nitrobenzene, and halogenated hydrocarbons such as tetrachloroethane. Of these solvents, acetic anhydride, acetic acid, pyridine or mixtures thereof are preferably used.

The amount of the orthocarboxylic ester added is about 0.3 to 10 moles per mole of Compound (i), preferably 0.3 to 1.0 mole. Thr reaction time is from 1 minute to 3 hours, preferably from 5 minutes to 1 hour. The reaction temperature is from 50° C. to the reflux temperature of the solvent used, preferably in the vicinity of 100° C.

Additionally there can be employed Method iii-[I-(2)] wherein Compound (i) and 2,6-di-tert-butyl-4-formylemethylene-4H-thiopyran are reacted by heating in a halogenated hydrocarbon such as 1,2,3-trichloropropane, Method iv-[I-(2)] wherein Compound (i) and methyldialkoxy acetate are reacted by heating in a solvent, etc. On the basis of the yield and ease of handling of the starting materials, Method i-[I-(2)] is most preferred.

Further, in producing thiopyrylium salts using benzoyl chloride and p-bromobenzyl chloride, the method, herein 2,6-di-tert-butyl-4-(methyl)thiopyrylium salt is reacted by heating in pyridine is preferable.

The thiopyrylium salt of this invention which is represented by Formula I-(3) is obtained by reacting the 2,6-di-tert-butyl-4-methylithiopyrylium salt of Formula (i) and 4-dialkylaminobenzaldehyde having 1 to 4 carbon atoms in the alkyl moiety such as 4-diethylaminobenzaldehyde and 4-dimethylaminobenzaldehyde.

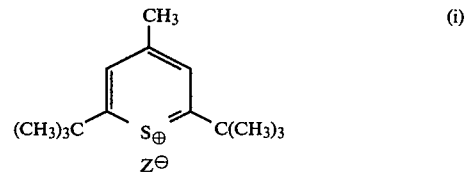

wherein $Z^\ominus$ represents an anion.

The amount of 4-dialkylaminobenzaldehyde used is 0.5 to 10 moles per mole of Compound (i), preferably 1 to 2 moles.

The reaction of Compound (i) and 4-dialkylaminobenzaldehyde is carried out by any one of the following two methods:

Method (A) wherein the reaction is carried out in the presence of an amine. Various solvents can be used in this reaction, including alcohols such as ethanol, nitriles such as acetonitrile, ketones such as methyl ethyl ketone, nitro compounds such as nitrobenzene, and halogenated hydrocarbons such as tetrachloroethane. Of these solvents, alcohols such as ethanol are preferably used.

Amines which can be used in this method include primary, secondary and tertiary alkyl amines containing 1 to 25 carbon atoms such as piperidine, triethylamine and hexylamine, aromatic amines containing 6 to 25 carbon atoms such as aniline and dimethylaniline and nitrogen-containing unsatuated heterocyclic compounds such as pyridine and quinoline.

The amount of the amine added is 0.1 to 10 moles per mole of the thiopyrylium salt, preferably 0.5 to 2 moles. In some cases, an excess of the amine is used as a solvent. The reaction time is from 30 minutes to 10 hours, preferably from 1 hour to 3 hours. The reaction temperature is from the vicinity of 50° C. to the reflux temperature of the solvent or amine, preferably in the vicinity of the reflux temperature. The amount of the solvent used is 1 to 100 ml per gram of Compound (i), preferably 3 to 10 ml.

Method (B) wherein the reaction is carried out in carboxylic acid anhydride. The acrboxylic acid anhydride, for example, acetic anhydride is added in an amount of 1 to 20 ml per gram of Compound of formula (i), preferably 2 to 10 ml. The reaction time is from 1 minute to 1 hour, preferably from 3 minutes to 10 minutes. The reaction temperature is from the vicinity of 80° C. to the reflux temperature (140° C.), preferably in the vicinity of 100° C.

The thiopyrylium salt represented by formula I-(4) is obtained by reacting 2,6-di-tert-butyl-4H-thiopyran-4-one represented by formula (iii) as illustrated below and an organometallic compound represented by formula (iv) as illustrated below and, thereafter, treating with an acid (Method i-[I-(4)]).

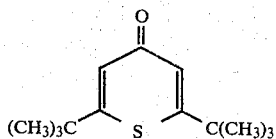

(iii)

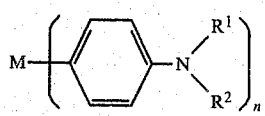

(iv)

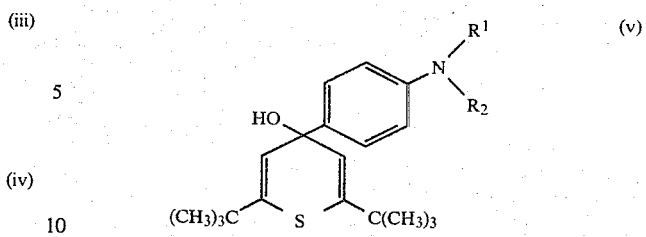

(v)

wherein M is a mono-, di- or tri-valent metal, a monohalogenated divalent metal or a dihalogenated trivalent metal. As such metals, MgBr, MgI, MgCl, CaL, Li, Na, K, Be and Al are preferred and MgBr and Li are most preferred. The $R^1$ and $R^2$ groups can be the same or different and include alkyl groups containing 1 to 4 carbon atoms as is described above.

Representative examples of the compounds represented by formula (iv) are 4-diethylaminophenylmagnesium bromide, 4-di-ethylaminophenylmangnesium chloride, 4-diethylaminophenyl lithium, 4-diethylaminophenyl sodium, tri(4-diethylaminophenyl)aluminum, di(4-diethylaminophenyl)berylium, 4-dimethylaminophenylmagnesium bromide, 4-dipropylaminophenylmagnesium chloride, and the like.

The reaction is preferably carried out in a solvent. Substantially water-free non-aqueous solvents can be used as the solvent. Examples of such solvents are ether compounds such as dimethyl ether, methyl ethyl ether, diethyl ether, dimethoxyethane, tetrahydrofuran and 1,4-dioxane, aromatic compounds such as benzene and toluene, and saturated hydrocarbon compounds such as pentane, hexane, cyclohexane, methylcyclohexane and petroleum ether.

In general, it is preferred that the reaction temperature is from −78° C. to the heat reflux temperature of the solvent used and that the reaction time is from 10 minutes to 3 hours. The most suitable reaction temperature and reaction time greatly depend on the types of the organometallic compound and solvent used. For example, where diethyl ether and 4-diethylaminophenylmagnesium bromide are used as the solvent and organometallic compound respectively, the reaction can be carried out at a reaction temperature ranging between about −20° C. and about 30° C. for a reaction time ranging between about 30 minutes and about 90 minutes.

The amount of the organometallic compound added is 1 mole to about 10 moles per mole of Compound of formula (iii), preferably 1 mole to about 3 moles. The reaction is preferably carried out in an oxygen-free atmosphere, e.g., by the term "oxygen-free atmosphere" is meant rare gases typified by helium and argon as well as inert gases typified by nitrogen. These gases replace air to form a substantially oxygen-free condition under which the reaction is carried out. The pressure of the rare gas or inert gas may be in the vicinity of atmospheric pressure, but this is just one example of the reaction pressure and suitable values may be selected depending on the case.

The compound obtained by treating Compound (iii) with the organometallic compound is 2,6-di-tert-butyl-4-hydroxy-4-(4'-disubstituted aminophenyl)-4H-thiopyran which is represented by formula (v):

wherein $R^1$ and $R^2$ are the same as defined above.

On immediately treating the reaction mixture as it is with the acid without isolating Compound of formula (v) therefrom, the dye of this invention is formed in high yields and precipitates in the solvent.

One of the major features of this invention resides in that the compound of this invention can be produced in high yields and the isolation of the compound is easy.

To activate the organometllic compound, hexamethylphophoric triamide, N,N,N',N'-tetramethylethylenediamine, 1,4-diazabicyclo 2,2,2 octane or the like can be added to the solvent.

Acids having a pKa of 5 or less, preferably 2 or less are useful for the production of the compound of this invention. Representative examples of such acids are hydrofluoric acid, hydrochloric acid, hydrobromic acid, hydroiodic acid, perchloric acid, periodic acid, tetrafluoroboric acid, hexafluorophosphoric acid, sulfuric acid, nitric acid, trifluoroacetic acid and p-toluenesulfonic acid. The fragment Z released from the acid (HZ) becomes the anion for Compound (I-(4)). The acid is added in an amount sufficient to obtain Compound (I-(4)) from Compound of formula (v), and it can be added in great excess.

One of the starting materials of this invention, 2,6-di-tert-butyl-4H-thiopyran-4-one (formula (iii)), is obtained by the same method as described hereinbefore.

Another starting material of this invention, the Compound of formula (iv), is generally obtained by reacting 4-diethylaminophenyl halide and a metal. For example, according to the method disclosed in Research Disclosure, 15742, page 79 (May 1977), 4-diethylaminophenylmagnesium bromide is produced from 4-diethylaminophenyl bromide and magnesium, and 4-diethylaminophenyllithium is produced from 4-diethylaminophenyl bromide and lithium.

Organometallic Compound (formula (iv)) is obtained by the method as described in Weygand & Hilgetag, Preparative Organic Chemistry, John Wiley & Sons, Inc. (1975), pages 748 to 809.

The thiopyrylium salt of this invention which is represented by formula (I-(4)) can also be obtained by reacting 2,6-di-tert-butyl-4H-thiopyran-4-one (formula (iii)) and diethylaniline in the presence of phosphorus pentaoxide and phosphorus oxychloride.

For the production of the thiopyrylium dye I-(4) of this invention, there can also be employed another method in which the 2,6-d-tert-butyl-4-(methylthio)thiopyrylium salt and the organometallic compound represented by formula (iv) are reacted and the resulting reaction product is then treated with an acid. However, from the point of yield and ease of handling, the reaction of compounds of the formulae (iii) and (iv) is preferred.

The thus obtained thiopyrylium dyes I-(1), I-(2), I-(3) and I-(4) are used as sensitizers for inorganic and organic photoconductor to improve the photoconductivity and sensitivity characteristics of the photoconductive substance.

Examples of inorganic photoconductive substances are zinc oxide and the like. However, particularly useful photoconductive substances are organic ones, for example, low moledular weight compounds, e.g., carbazoles such as carbazole and N-ethylcarbazole, triarylamines such as tri-p-tolylamine and triphenylamine, polyarylmethanes represented by the formula:

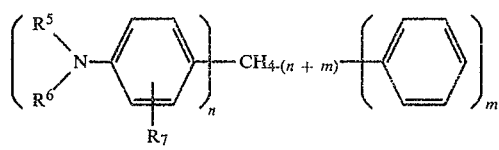

(wherein m is an integer of 2 to 4, n is an integer of 0 to 2, $n+m \leq 4$, $R^5$, $R^6$ and $R^7$ are each hydrogen, an alkyl group, e.g., methyl, ethyl or propyl, or an aryl group, e.g., phenyl or tolyl), condensed aromatic ring compounds such as anthracene, unsaturated bond-containing aromatic compounds such as tetraphenylbutadiene and tetraphenylhexatriene, and unsaturated heterocyclic ring-containing compounds such as oxadiazole, thiadiazole, triazole, imidazole, pyrazoline and their derivatives, and high molecular weight compounds, e.g., poly-N-vinylcarbazole derivatives such as poly-N-vinylcarbazole and brominated poly-N-vinylcarbazole, polyvinyl anthracene, polyacenaphthylene, polyvinyl acridine and polyvinyl phenothiadine.

Preferred among these photoconductive substances are unsaturated heterocyclic ring-containing compounds, representative examples of which are poly-N-vinyl carbazole, triarylamines such as tri-p-tolylamine and triphenylamine, polyarylmethane such as 4,4-bis-(diethylamino)-2,2'-dimethyltriphenylmethane, and pyrazoline derivatives such as 3-(4-dimethylaminophenyl)-1,5-diphenyl-2-pyrazoline.

The photoconductive composition of this invention containing Thiopyrylium Dye I-(1), I-(2), I-(3) or I-(4) as a sensitizer is obtained by dissolving the thiopyrylium dye and photoconductive substance in an organic solvent. The solution thus obtained is coated on an electrically conductive support by a usually employed method, e.g., rotary coating, blade coating, knife coating, reverse roll coating, dip coating, rod bar coating or spray coating and then dried to produce a light-sensitive material. Alternatively the solution is sprayed by use of a minispray apparatus to produce particles and these particles are then dispersed in an insulative liquid to form a dispersion. This dispersion is used in the photoelectrophoretic method.

Examples of such electrically conductive supports are paper, an aluminum-paper laminate, metal foils such as an aluminum foil and a zinc foil, a metal plate of aluminum, copper, zinc, brass or the like and a zinc-plated plate, those obtained by vapor-depositing a metal such as chromium, silver, nickel or aluminum on a usual photographic film base such as paper, a cellulose acetate film, a polystyrene film or the like, etc. Preferred supports are those prepared by vapor-depositing a metal such as chromium, silver, nickel, aluminum or indium oxide on paper, a cellulose acetate film or a polyethyleneterephthalate film.

Volatile hydrocarbon solvents having a boiling point of 200° C. or less are used as an organic solvent. In particular, halogenated hydrocarbons containing 1 to 3 carbon atoms, such as dichloromethane, chloroform, dichloroethane, tetrachloroethane, dichloropropane and trichloroethane are preferred. Additionally, various solvents for use in coating compositions, such as aromatic hydrocarbons such as chlorobenzene, toluene, xylene and benzene, ketones such as acetaone and 2-butanone, ethers such as tetrahydrofuran, and methylene chloride, can be used singly or in combination with each other. The solvent is added in an amount of about 1 to 100 g, preferably 5 to 20 g, per gram of the total weight of the dye, photoconductor and other additives.

The amount of the sensitizer added is about 0.0001 to 30 parts by weight, preferably 0.001 to 10 parts by weight, per 100 parts by weight of the photoconductor.

In an embodiment of the use of the present composition, the sensitizer is preferably incorporated into the particles to be used in the photoelectrophoretic method. The photoelectrophoretic method using these particles permits the formation of color images having excellent three color separation.

The particles having $1\mu$ to $10\mu$ in diameter for use in the photoelectrophoretic method are produced by use of a minispray apparatus from a solution containing the photoconductive substance as described above, e.g., poly-N-vinylcarbazole and the sensitizer of this invention wherein the solution contains the photoconductive substances in an amount of 0.1 to 10% by weight. These particles are further dispersed in an insulative liquid containing a saturated hydrocarbon, such as decane, dodecane, octane, paraffin and isooctane, preferably in a long chain alkylhydrocarbon, e.g., Isopar E, Isopar H, Isopar G (produced by Esso Chemical Co.), etc. in an amount to contain 1 to 2% by weight of particles in the insulative liquid. The thus obtained dispersion is used in the photoelectrophoretic method. Isopar E, Isopar H and Isopar G contain 99.9, 99.3 and 99.8% by weight, respectively, of a saturated hydrocarbon and 0.05, 0.2 and 0.2% by weight, respectively, of an aromatic hydrocarbon. Isopar H, however, contains olefin of 0.5% by weight or less. The respective boiling temperatures are 115° C. to 142° C., 174° C. to 189° C. and 158° C. to 177° C. The amount of the particles in the dispersion is 0.5 to 10% by weight, preferably 1 to 3% by weight based upon the weight of the dispersion. The photoelectrophoretic method and the apparatus for use therein are described in Japanese Patent Publication No. 20640/70.

Consequently, unlike photosensitive particles prepared by using the conventional thiopyrylium dyes, photosensitive particles for color photoelectrophoretic electrophotography that contain the new type of thiopyrylium dyes as a spectral sensitizer provide improved color separation from blue sensitive yellow particles. Color photoelectrophoretic electrophotographic processing of a mixture of three-colored particles comprising yellow and magenta particles plus a cyan particle that contains Compound I-(2) or I-(3) as a sensitizing dye for the red region provides an image exhibiting distinct color separation from the yellow particles.

Magenta particles containing Compound I-(1) or I-(4) as a sensitizer for the green region provides an image exhibiting distinct color separation from the yellow particles.

It has further been found that the use of novel thiopyrylium dyes having 2,6-di-tert-butylthiopyrylium nucleus as a sensitizer for a photoconductive substance, particularly an organic photoconductive substance, e.g., poly-N-vinyl carbazole, triarylamine or triarylmethane permits to provide photoconductive materials having higher sensitivities than do the conventional thiopyrylium dyes having 2,6-diphenylthiopyrylium nucleus. For example, the novel thiopyrylium dyes as illustrated hereinafter, i.e., Dyes I-(1)', I-(2)', I-(3)' and I-(4)' provide photoconductive materials having higher sensitivities than the conventional thiopyrylium dyes I-(1)'', I-(2)'', I-(3)'' and I-(4)''. While the reasons for this are not still elucidated, it is partly considered that the tert-butyl groups of the novel thiopyrylium compounds increase the mutual solubility thereof with the organic photoconductive substance.

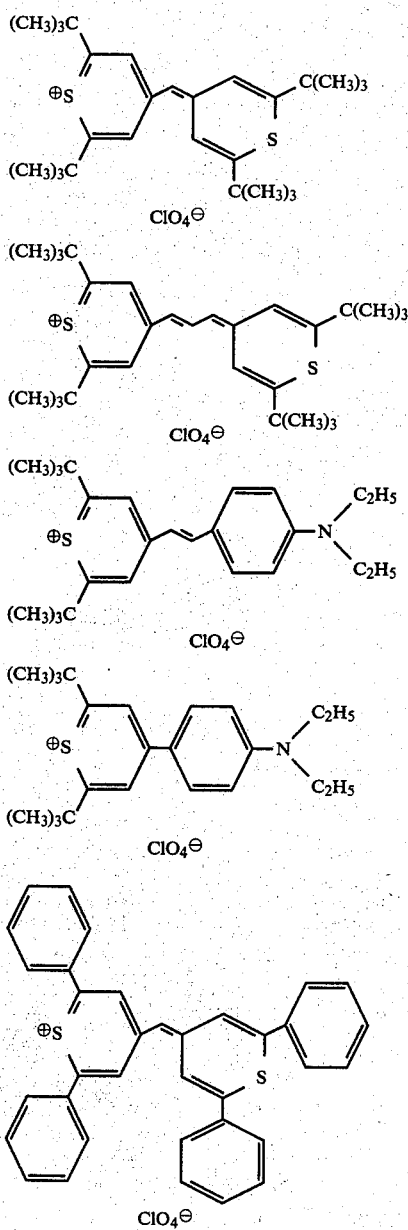

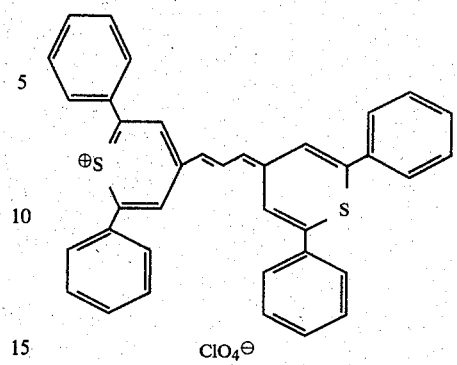

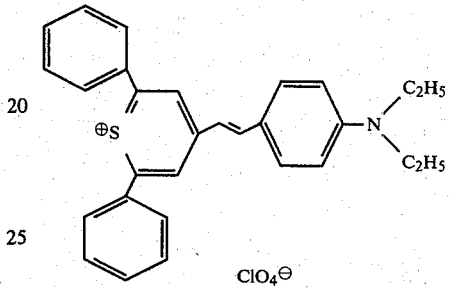

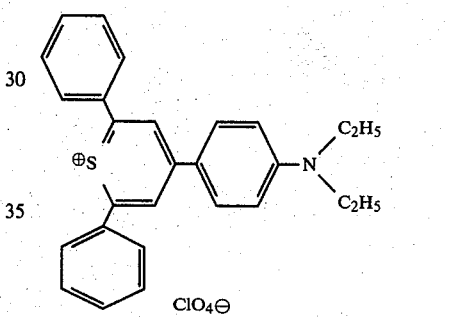

Suitable additives can be added to the photoconductive layer and particles to improve the properties thereof.

For example, in the photoconductive composition of this invention can be incorporated an electrically insulative binder component. Binders preferably used in the formation of the photoconductive composition of this invention are those film-forming and hydrophobic polymer binders which have very high insulating strengths and good electrically insulating properties. Examples of such substances are vinyl resins; natural resins such as gelatin, a cellulose ester derivative and cellulose nitrate; polycondensates including polyester and polycarbonate; a silicon resin; an alkyd resin including a styrene-alkyd resin, etc.; paraffin; various mineral waxes, etc.

Useful polymer binders are described in *Research Disclosure*, Vol. 109, pages 61 to 67, under the title of *Electrophotographic Element, Material and Method*.

In general, the amount of the binder present in the photoconductive composition of this invention is not critical. Typically, the effective amount of the binder is in the range of from about 10% by weight to about 90% by weight based upon the total weight of the photoconductive material and the binder.

In the production of photoconductive particles, an electric charge controlling agent and a dispersion stabilizer can be added. In particular, a lauryl methacrylate-styrene (4 to 2:1) copolymer and a 2-ethylhexyl methacrylate-styrene (4:2 to 1) copolymer, which have both of the electric charge controlling and dispersion stabilizing functions, are advantageously used.

In order to increase the flexibility and strength, a plasticizer, e.g., chlorinated diphenyl, dimethyl phthalate and an expoxy resin (trade name: Epikote) can be added in an amount of 60 parts by weight or less, preferably 10 to 40 parts by weight per 100 parts by weight of the photoconductive substance.

The thickness in which the photoconductive composition of this invention is coated on an appropriate support can vary widely. Usually, the thickness of the composition coated (before the drying) in the range of from about 10 microns to about 300 microns is sufficient for the practice of this invention. The preferred thickness before the drying has been found to be in the range of from about 50 microns to about 150 microns. However, outside of this range, useful results can be obtained.

The thickness after the drying is sufficient to be in the range of from about 2 microns to about 50 microns. However, between about 1 micron and about 200 micron, useful results are obtained.

FIGS. 1, 2, 3, and 4 are spectral sensitivity spectra of the compositions containing respectively novel thiopyrylium dyes of this invention: I-(1)′, I-(2)′, I-(3)′ and I-(4)′ as a sensitizer for poly-N-vinyl carbazole. On the other hand, FIGS. 5, 6, 7 and 8 are spectral sensitivity spectra of the compositions containing respectively the conventional thiopyrylium dyes: I-(1)″, I-(2)″, I-(3)″ and I-(4)″ as a sensitizer for poly-N-vinyl carbazole.

Comparisons between FIGS. 1, 2, 3 and 4 and FIGS. 5, 6, 7 and 8 clearly indicate that the novel thiopyrylium dyes show no sub-absorption in the vicinity of 400 nm unlike the conventional dyes containing the aryl group since they have the tert-butyl groups at the 2- and 6-positions of the thiopyran ring, and therefore the photoconductive composition containing the novel thiopyrylium dye as the spectral sensitizer is not sensitive to blue light in the visible region, particularly to light of 400 nm to 450 nm.

The thiopyrylium dye of this invention is effective in xerography, electrofax type electrophotography and photoelectrophoretic electrophotography. In particular, it is useful in the color electrophotography using photoconductive particles. However, this invention is not limited thereto.

The following examples and comparative examples are given to illustrate this invention in greater detail.

EXAMPLE 1

Preparation of 2,6-di-tert-Butyl-4-(2,6-di-tert-butyl-4H-thiopyran-4-ylidenemethyl)thiopyrylium Perchlorate [I-(1)′]

(i) 34.6 g of 2,6-di-tert-Butyl-4H-pyran-4-one was dissolved in 240 ml of anhydrous benzene, and 73 g of phosphorus pentasulfide was added thereto. The mixture was heated at the reflux temperature for 2.5 hours while stirring.

After completion of the reaction, the benzene solution was removed by decantation. Aqueous ammonia was added to the residue to decompose the phosphorus pentasulfide, followed by extracting with diethyl ether and drying over anhydrous sodium sulfate. The solvent was distilled off under reduced pressure from the benzene solution, and the residue was extracted with hexane and concentrated to obtain 16.0 g of reddish crystals. The ethereal extract and an oily material having not been extracted with hexane were combined and passed through a silica gel column to thereby purify the product. Additionally, 6.8 g of crystals were obtained.

Thus, 2,6-di-tert-butyl-4H-pyran-4-thione was obtained. Total yield: 22.8 g (61%); m.p.: 108°–108.5° C.; crystal: tint colored (recrystallized from hexane).

6.64 g of 2,6-di-tert-butyl-4H-pyran-4-thione was dissolved in 330 ml of hexamethylphosphoric triamide, and an argon gas was passed therethrough for 20 minutes.

The mixture was stirred on an oil bath at 85°–90° C., and 19.8 g of sodium hydrosulfide [prepared by vacuum drying about 70% NaSH XH$_2$O (a product of Wako Pure Chemical Industries, Ltd.) over phosphorus pentoxide at 70°–90° C. for one day] was added thereto in an argon atmosphere over a period of 30 minutes.

The stirring was continued at the same temperature for 1.5 hours, and the reaction solution was thrown into water whereby the reaction completed. The thus formed crystal was filtered, dried and recrystallized from hexane.

Thus, 2,6-di-tert-butyl-4H-thiopyran-4-thione was obtained. Yield: 1.78 g (25%); m.p.: 162° C.; crystal; red.

1.55 g of 2,6-di-tert-butyl-4H-thiopyran-4-thione was mixed with 20 ml of acetone and 5 ml of methyliodide, and the mixture was refluxed for 1 hour. The solvent was distilled off under reduced pressure and the recrystallization of the residue from acetone provided 1.55 g of prismatic crystals. This was confirmed to be 2,6-di-tert-butyl-4-(methylthio)thiopyrylium iodate (Compound of formula (ii)). Yield: 63%; m.p.: 150° C. to 155° C. (decomposition).

Elemental Analysis: Calculated for: C$_{14}$H$_{23}$S$_2$I: C 43.98%, H 6.06%, S 16.77%. Found: C 43.87%, H 6.14%, S 16.53%.

I.R. Spectrum (wave number cm$^{-1}$): 1567, 1475, 1118

N.M.R. Spectrum: (Chemical shift, ppm, trimethylsilane) (proton) 99.6 MHz in deuterodimethylsulfoxide 1.59, 3.06, 8.44 (each singlet, area ratio=18:3:2) (carbon 13) 25.5 MHz in deuterodimethylsulfoxide 177.13, 172.29, 126.89, 41.01, 30.19, 15.50.

U.V. and Visible Spectrum: (wave length nm, log ε in parentheses, in chloroform) 271(3.95), 303(3.68), 365(4.35), 482(2.95).

(ii) The 2,6-di-tert-butyl-4-(methylthio)thiopyrylium iodide as obtained above in the amount of 1.30 g was mixed with 10 ml of dimethylsulfoxide and 1 ml of water, and the mixture ws stirred while heating on an oil bath maintained at 85°–90° C.

The reaction solution was poured in water and extracted with diethyl ether. The diethyl ether solution was dried over anhydrous sodium sulfate, and then the solvent was distilled off under reduced pressure. By passing the residue through an alumina column by use of a mixed solvent of benzene and diethyl ether (1:1 by volume), 740 mg of crystals were obtained. Yield: 97%; recrystallization from cyclohexane. Thus, 2,6-di-tert-butyl-4H-thiopyran-4-one (colorless crystal, m.p. 97°–98° C.) was obtained.

Elemental Analysis: Calculated for: C$_{13}$H$_{20}$SO: C 69.59%, H 8.99%, S 14.29%. Found: C 69.13%, H 9.06%, S 14.41%.

Mass Analysis (m/e): 224 (30%), 181 (100%).

I.R. Spectrum (wave number cm$^{-1}$): 1610, 1348, 880, 730.

N.M.R. Spectrum: (chemicl shift, ppm, trimethylsilane) (proton) 99.6 MHz in deuterochloroform 1.38, 6.90 (each singlet, area ratio=9:1 (carbon 13) 25.5 MHz in deuterochloroform 183.00, 165.38, 124.32, 38.38, 30.54.

U.V. and Visible Spectrum: (wave length nm, log ϵ in parentheses, in cyclohexane) 222(3.85), 285(4.17), 329(1.57), 363(0.96).

550 mg of the compound was dissolved in 20 ml of diethyl ether, and while keeping the solution at about $-10°$ C., 8.6 ml of a diethyl ether solution of methylmagnesium iodide (2.7 millimols) was dropped therein. After all the diethyl ether solution was dropped, the resulting mixture was stirred for 45 minutes at room temperature (about 23° C.), and then a saturated ammonium aqueous solution was added. After the decantation of the ether solution, the ether was distilled off under reduced pressure, and 20 ml of 35% perchloric acid was added. On warming the mixture on a bath, crystals precipitated. These crystals were filtered, washed with cold water, further washed with diether ether and dried. The yield was 470 mg. The recrystallization of the product from ethanol provided 2,6-di-tert-butyl-4-methylthiopyrylium perchlolate (Compound of formula (i)) (m.p. 192°–193° C., colorless crystal).

Elemental Analysis: Calculated for: $C_{14}H_{23}ClO_4S$: C 52.08%, H 7.18%, S 9.93%. Found: C 52.00%, H 7.28%, S 9.75%.

I.R. Spectrum (wave number $cm^{-1}$): 1590, 1375, 1085.

N.M.R. Spectrum: (chemical shift, ppm, trimethylsilane) (proton) 99.6 MHz in deuteroacetone 1.67, 2.96, 8.81 (each singlet, area ratio=18:3:2) (carbon 13) 25.5 MHz in deuteroacetone 184.87, 167.08, 134.67, 42.53, 31.18, 28.75.

U.V. and Visible Spectrum: (wave length nm, log ϵ in parentheses, in acetonitrile) 302(3.97), 262(3.88), 213(4.47).

(iii) 200 mg of 2,6-di-tert-butyl-4-methylthiopyrylium perchlorate and 230 mg of 2,6-di-tert-butyl-4(methylthio)tiopyrylium iodide were mixed in 1 ml of acetic anhydride and stirred at 100° C. for 30 minutes. The mixture was allowed to cool and the crystals obtained were filtered. The recrystallization of the crystals from ethyl acetate provided Compound of formula (I)-(1). Yield: 135 mg; m.p.: 195°–198° C.

Elemental Analysis: Calculated for: $C_{27}H_{41}S_2ClO_4$: C 61.28%, H 7.81%, S 12.11%. Found: C 60.99%, H 7.85% S 12.40%.

I.R. Spectrum (wave number $cm^{-1}$): 1567, 1480, 1090.

N.M.R. Spectrum: (chemical shift, ppm, trimethylsilane, in deuteroacetone, 24° C.) 1.53, 7.81, 8.49 (each singlet, area ratio=36:4:1).

U.V. and Visible Spectrum: (wave length nm, log ϵ in parentheses, in acetonitrile) 573(72,000), 536(23,700), 360(6,400), 295(17,700), 249(15,600).

EXAMPLE 2

1 g of Poly-N-vinyl carbazole and 3 mg of Compound I-(1)′ obtained in Example 1 were dissolved in 10 g of 1,2-dichloroethane, and the solution so obtained was coated with a No. 16 rod bar on a polyester film on which aluminum had been vapor deposited. It was dried at 55° C. for one day to produce a light-sensitive material.

This light-sensitive material was charged to +450 V by application of +6 kV coona discharge by use of an apparatus on the market and then exposed to light with a tungusten lamp so that the intensity of illumination on the surface be 4.5 lux. By measuring the time (seconds) required until the surface potential was 225 V, the exposure amount was obtained. The exposure amount was found to be E ½=67 lux second.

COMPARATIVE EXAMPLE 1

The same procedure as in Example 2 was followed except that Compound I-(1)″ defined above was used in place of Compound I-(1)′, to thereby produce a light-sensitive material. This light-sensitive material was measured by the same method as in Example 2, with the results as illustrated in Table 1.

Comparative Example 1 containing the known thiopyrylium dye I-(1)″ was used as a control for comparing with Example 2.

TABLE 1

|  | Compound | E ½ (lux second) |
|---|---|---|
| Example 2 | I-(1)′ | 67 |
| Comparative Example 1 | I-(1)″ | 83 |

EXAMPLE 3

Production of 2,6-di-tert-Butyl-4-[3-(2,6-di-tert-butyl-4H-thiopyran-4-ylidene)propene-1-yl]thiopyrylium Perchlorate (Compound I-(2)′)

A mixture of 0.2 g of 2,6-di-tert-butyl-4-methylthiopyrylium perchlorate (Compound of formula (i)) as obtained in Example 1 and 0.15 g of diphenylformamidine was heated in a test tube at 165° C. for 5 minutes, and then 0.2 g of Compound (i), 0.2 g of sodium acetate and 1 ml of acetic anhydride were added thereto. The resulting mixture was heated at 165° C. for 5 minutes and then allowed to cool. Diethyl ether was added, and crystals were filtered, washed with water and dried. The recrystallization of the crystals from ethyl acetate provided 0.128 g of the crystals of 2,6-di-tert-butyl-4-[3-(2,6-di-tert-butyl-4H-thiopyran-4-ylidene)-propene-1yl]thiopyrylium perchlorate (yield: 36%, m.p.: 226°–227° C.).

Elemental Analysis: Calculated for: $C_{29}H_{43}S_2ClO_4$: C 62.73%, H 7.81%, S 11.55%. Found: C 62.61%, H 7.79%, S 11.09%.

I.R. Spectrum (wave number $cm^{-1}$): 1500, 1272, 1175, 730.

N.M.R. Spectrum: (chemical shift, ppm, trimethylsilane, in deuteroacetone, 24° C.) 1.49 (singlet), 6.61 (doublet), 7.85 (singlet), 8.82 (triplet) Area ratio=18:2:4:1.

U.V. and Visible Spectrum: (wave length nm, (ϵ), in acetonitrile). 694(214,000), 645(74,900), 380(2,700), 313(12,700), 232(11,100).

EXAMPLE 4

1 g of poly-N-vinyl carbazole and 3 mg of Compound I-(2)′ as obtained in Example 3 were dissolved in 10 g of 1,2-dichloroethane, and the solution so obtained was coated with a No. 16 rod bar on a polyester film on which aluminum had been vapor deposited. It was dried at 55° C. for one day to obtain a light-sensitive material. This light-sensitive material was charged to 450 V by application of 6 kV corona discharge by use of an apparatus on the market and then exposed to light with a tungusten lamp so that the intensity of illumination on the surface by 4.5 lux. By measuring the time (seconds) required until the surface potential was 225 V, the exposure amount was obtained. As a result, E ½ = 31 lux second.

COMPARATIVE EXAMPLE 2

The same procedure as in Example 4 was followed except that Compound I-(2)″ defined above was used in place of Compound I-(2)′, to thereby obtain a light-sensitive material. This light-sensitive material was measured in the same manner as in Example 4, with the results as illustrated in Table 2. Comparative Example 2 wherein the known thiopyrylium dye I-(2)″ was used is a control for comparing with Example 4.

TABLE 2

| | Compound | E ½ (lux sec.) |
|---|---|---|
| Example 4 | I-(2)′ | 31 |
| Comparative Example 2 | I-(2)″ | 55 |

EXAMPLE 5

Production of 2,6-di-tert-Butyl-4-[3-(2,6-di-tert-butyl-4H-thiopyran-4-ylidene)propene-1-yl]thiopyrylium Perchlorate (Compound I-(2)′)

0.14 g of 2,6-di-tert-butyl-4-methylthiopyrylium perchlorate (Compound of formula (i)) and 0.10 g of diphenylformamidine were mixed with 0.08 g of piperidine, and the mixture was heated in 5 ml of ethanol at the reflux temperature for 1 hour. After the mixture was allowed to cool, diethyl ether was added thereto. Crystals were filtered, washed with water, dried and then recrystallized from ethyl acetate. Yield: 0.08 g; m.p.: 225°–226° C. The I.R. spectrum and N.M.R. spectrum of this compound were the same as those of the compound as obtained in Example 3.

EXAMPLE 6

Production of 2,6-di-tert-Butyl-4-[3-(2,6-di-tert-butyl-4H-thiopyran-4-ylidene)propene-1-yl]thiopyrylium Perchlorate (Compound I-(2)′)

Compound of formula (i) as obtained in Example 1 in the amount of 160 mg was dissolved in 1 ml of acetic anhydride, and 45 mg of ethyl orthoformate was added thereto. The resulting mixture was heated with stirring at 85° C. for 10 minutes and then allowed to cool. Diethyl ether was added, and crystals were filtered. On recrystallizing the crystals from ethyl acetate, 53 mg of crystals were obtained. Yield: 20%; m.p.: 226° C.

The I.R. spectrum and N.M.R. spectrum of this crystal were the same as those of the crystal as obtained in Example 3.

EXAMPLE 7

Production of 2,6-di-tert-Butyl-4-[3-(2,6-di-tert-butyl-4H-thiopyran-4-ylidene)-2-phenylpropane-1-yl]thiopyrylium Tetrafluoroborate (Compound I-(2))

310 mg of 2,6-dimethyl-4-methylthiopyrylium tetrafluoroborate and 80 mg of benzoyl chloride were heated in pyridine for 30 minutes on an oil bath maintained at 120° C. After the heated mixture was allowed to cook, the crystal was obtained from 50 ml of diethyl ether. The recrystallization of the crystals provided 30 mg of Compound I-(2) (m.p.: 249°–250° C.).

Elemental Analysis: Calculated for: $C_{35}H_{47}S_2BF_4$: C 67.93%, H 7.66%, S 10.36%. Found: C 67.76%, H 7.65%, S 10.09%.

I.R. Spectrum: (wave number cm$^{-1}$) 1588, 1467, 1413, 1233, 1180, 1080.

U.V. and Visible Spectrum: (wave length nm, (ε) in acetonitrile). 705(112,000), 360(15,600), 308(10,200).

EXAMPLE 8

Production of 2,6-di-tert-butyl-4-[3-(2,6-di-tert-butyl-4H-thiopyran-4-ylidene)-2-(4-bromophenyl)propene-1-yl]tiopyrylium Tetrafluoroborate (Compound I-(2))

310 mg of 2,6-dimethyl-4-methylthiopyrylium tetrafluoroborate and 110 mg of p-bromobenzoyl chloride were heated in pyridine for 40 minutes on an oil bath maintained at 120° C. After allowing to cool, diethyl ether was added thereto to precipitate crystals and the crystals thus obtained were recrystallized from ethylacetate. Yield: 20 mg; m.p.: 247°–248° C.

Elemental Analysis Calculated for: $C_{13}H_{20}SO$: C 60.29%, H 6.64%, S 9.19%. Found: C 60.01%, H 6.48%, S 9.34%.

I.R. Spectrum: (wave number cm$^{-1}$) 1588, 1460, 1413, 1235, 1190, 1080.

U.V. and Visible Spectrum: (wave length nm, (ε) in acetonitrile) 706(100,000), 365(18,900), 308(12,900).

EXAMPLE 9

Production of 2,6-di-tert-butyl-4-[4-(diethylamino)styryl]thiopyrylium Perchlorate [Compound I-(3)′]

0.496 g of 2,6-di-tert-butyl-4-methylthiopyrylium perchlorate as obtained in Example 1 and 0.26 g of 4-diethylaminobenzaldehyde were heated in 1.5 ml of acetic anhydride at 95° C. for 7 minutes. After allowing to cool, diethyl ether was added to precipitate crystals. These crystals were filtered and recrystallized from ethanol. Yield: 0.404 g; needle crystal; m.p.: 218°–219° C.

The elemental analysis and the spectra confirmed that this was 2,6-di-tert-butyl-4-[4-(diethylamino)styryl]thiopyrylium perchlorate.

Elemental Analysis: Calculated for: $C_{25}H_{36}NSO_4Cl$: C 62.28%, H 7.52%, N 2.90%, S 6.65%. Found: C 62.26%, H 7.55%, N 3.05%, S 6.74%.

I.R. Spectrum: (wave number cm$^{-1}$) 1552, 1515, 1183, 1152.

N.M.R. Spectrum: (chemical shift, ppm, trimethylsilane, in deutrechloroform) 1.24 (t, 6H, J=7.08), 1.55 (s, 18H), 3.49 (q, 4H, J=7.08), 6.74 (d, 2H, J=9.28), 7.85 (d, 2H, J=9.28), 7.31 (d, 1H, J=15.1), 8.13 (d, 1H, J=15.1), 8.12 (s, 2H).

U.V. and Visible Spectrum: (wave length nm, (ε), in acetonitrile) 622(82,900), 350(6,100), 310(11,600).

EXAMPLE 10

1 g of poly-N-vinylcarbazole and 3 mg of Compound I-(3)′ as obtained in Example 9 were dissolved in 10 g of 1,2-dichloroethane, and the solution so obtained was coated with a No. 16 rod bar on a polyester film on which aluminum has been vacuum evaporated. It was dried at 55° C. for one day to produce a light-sensitive material. This light-sensitive material was charged to +450 V by application of +6 kV by use of an apparatus on the market and exposed to light with a tungusten lamp so that the intensity of illumination on the surface be 4.5 lux. The time (seconds) required until the surface potential was 225 V was measured to obtain the exposure amount. As a result, $E_{\frac{1}{2}}=27$ lux sec.

COMPARATIVE EXAMPLE 3

The same procedure as in Example 9 was followed except that Compound I-(3)" as illustrated in Table 3 was used in place of Compound I-(3)', to thereby produce a light-sensitive material. This light-sensitive material was measured in the same manner as in Example 9, with the results as illustrated in Table 3.

Comparative Example 3 wherein the known thipyrylium dye: I-(3)" was used is a control for comparing with Example 10.

TABLE 3

| | Compound | $E_{\frac{1}{2}}$ (lux sec.) |
|---|---|---|
| Example 10 | I-(3)' | 27 |
| Comparative Example 3 | I-(3)" | 37 |

EXAMPLE 11

0.25 g of 2,6-di-tert-butyl-4-methylthiopyrylium perchlorate (Compound of formula (i)) and 0.14 g of 4-diethylaminobenzaldehyde were added to 5 ml of ethanol, and moreover 70 mg of piperidine was added thereto.

The mixture was reacted by heating at the reflux temperature (about 78° C.) for 3 hours and then allowed to cool. By adding diethyl ether, crystals were precipitated. These crystals were filtered and recrystallized from ethanol whereupon 0.15 g of needle crystals having a melting point of 218° C. were obtained.

The I.R. spectrum and N.M.R. spectrum of this crystal were the same as those of the compound as obtained in Example 9.

EXAMPLE 12

Production of 2,6-di-tert-butyl-4-[4-(dimethylamino)styryl]thiopyrylium Perchlorate [Compound I-(3)']

319 mg of 2,6-di-tert-butyl-4-methylthiopyrylium perchlorate and 150 mg of 4-dimethylaminobenzaldehyde were heated in 5 ml of acetic anhydride for 40 minutes on an oil bath maintained at 100° C. After allowing to cool, diethyl ether was added to precipitate crystals and then the crystals were recrystallized from ethanol. Yield: 210 mg; m.p.: 240° C.

Elemental Analysis: Calculated for: $C_{23}H_{32}NSClO_4$: C 60.85%, H 7.10%, N 3.09%. Found: C 60.91%, H 7.05%, N 3.22%.

I.R. Spectrum: (wave number $cm^{-1}$) 1552, 1528, 1187, 1160, 1120.

U.V. and Visible Spectrum: (wave length nm, ($\epsilon$) in acetonitrile) 610(68,100), 310(11,800).

EXAMPLE 13

Production of 2,6-di-tert-butyl-4-[4-(diethylamino)phenyl]thiopyrylium Perchlorate [Compound I-(4)']

0.206 g of 2,6-di-tert-butyl-4H-thiopyran-4-one prepared in a stream of argon by the same method as in Example 1 was dissolved in 30 ml of diethyl ether, and the solution was cooled to 0° C. In this solution was dropped 4 ml of a tetrahydrofuran solution containing 2 millimoles of 4-diethylaminophenylmagnesium bromide over 30 minutes.

After the completion of the dropping, the mixture was stirred for 1 hour at a room temperature, and the thus formed reaction solution was poured in 100 ml of a 2% aqueous solution of perchloric acid. The crystals formed were filtered, washed with water and dried. Recrystallization from ethyl acetate provided Compound I-(4)'.

Yield: 0.327 g.

Melting Point: needle-like crystal, 217°-218° C.

Elemental Analysis: Calculated for: $C_{23}H_{34}NSClO_4$: C 60.57%, H 7.51%, N 3.07%, S 7.03%. Found: C 60.59%, H 7.58%, N 3.05%, S 7.12%.

I.R. Spectrum: (wave number $cm^{-1}$) 1560, 1275, 1213, 1090.

N.M.R. Spectrum: (chemical shift, ppm, trimethylsilane, in deutrechloroform) (s, d, t and q in the parentheses indicate respectively singlet, doublet, triplet and quaterlet; the figure before H indicates the area ratio; and J indicates a bond constant (unit: Herz).)

1.28 (t, 6H, J=7.08), 1.60 (s, 18H), 3.56 (q, 4H, J=7.08), 6.93 (d, 2H, J=9.28), 8.06 (d, 2H, J=9.28), 8.34 (s, 2H).

U.V. and Visible Spectrum: (wave length nm, ($\epsilon$) in actonitrile) 532(62,200), 288(11,300), 259(7,700).

EXAMPLE 14

1 g of poly-N-vinyl carbazole and 3 mg of Compound I-(4)' as obtained in Example 13 were dissolved in 10 g of 1,2-dichloroethane, and the solution was coated with a No. 16 rod bar on a polyester film on which aluminum had been vacuum evaporated. It was dried at 55° C. for one day to produce a light-sensitive material.

This light-sensitive material was charged to +450 V by application of +6 kV corona discharge by use of an apparatus on the market and then exposed to light with a tungusten lamp so that the intensity of illumination on the surface be 4.5 lux. The time (seconds) required until the surface potential was 225 V was measured. As a result, $E_{\frac{1}{2}}=47$ lux sec.

COMPARATIVE EXAMPLE 4

The same procedure as in Example 13 was followed except that Compound I-(4)" was used in place of Compound I-(4)', to thereby produce a light-sensitive material. This light-sensitive material was measured in the same manner as in Example 14, with the results as illustrated in Table 4.

Comparative Example 4 wherein the known thiopyrylium dye: I-(4)" was used is a control for comparing with Example 14.

TABLE 4

| | Compound | $E_{\frac{1}{2}}$ lux sec. |
|---|---|---|
| Example 11 | I-(4)' | 47 |
| Comparative Example 4 | I-(4)" | 55 |

EXAMPLE 15

From a solution consisting of 5 g of poly-N-vinyl carbazole, 150 mg of a dye and 250 g of dichloromethane were produced particles by use of a minispray apparatus (produced by Yamato Kagaku Co.). As the dye, the three dyes as illustrated below were used to produce the corresponding three color particles.

Cyan Particle: 2,6-di-tert-butyl-4-[3-(2,6-

| | di-tert-butyl-4H-thiopyran-4-ylidene)propene-1-yl]thiopyrylium perchlorate [Compound I-(2)'] |
|---|---|
| Magenta Particle: | Rhodamine B |
| Yellow Particle: | Thioflavine T |

Figure 9:
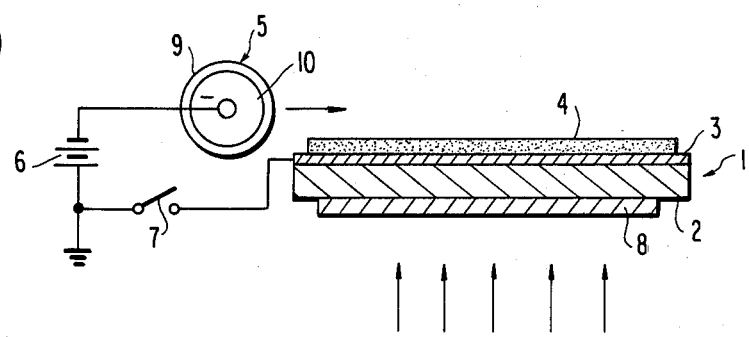
FIG. 9 illustrates a photoelectrophoretic photographing apparatus.

A mixture of these three colored particles was dispersed in 250 ml of Isopar H (insulative liquid consisting of 99.3% by weight of a saturated hydrocarbon, 0.2% by weight of an aromatic hydrocarbon and 0.5% by weight or less of olefin; m.p.: 174° C. to 189° C.; produced by Esso Chemical Co., Ltd.), which contained 1 g of a lauryl methacrylate-styrene (4:1) copolymer (viscosity: 1.52; specific gravity: 0.86) for the dispersion stability and electric charge control of the particles, in a concentration of 2% by weight to produce a dispersion for photoelectrophoresis. To form images by using the dispersion, the photoelectrophoretic photographing apparatus as illustrated in FIG. 9 was employed. The reference numeral 1 indicates a transparent electrode which comprises an optically transparent glass layer 2 covered by an optically transparent tin oxide thin layer 3 (available on the market under the trade name of NESA). 4 indicates a dispersion for photoelectrophoresis and 5 indicates a rejection electrode which is connected through a switch 7 to an electric source 6. 8 indicates a color slide; 9, a rejection electrode material layer; and 10, an electrically conductive central core. The electrode 5 is in the form of roll with the electrically conductive central core 10 connected to the electric source 6.

The roll has a diameter of about 6.5 cm and travels along the plate at a speed of about 2 cm/sec. The arrow indicates the direction of light. Light is irradiated so that the intensity of illumination on the surface of the NESA glass be 20,000 lux. The voltage applied is 1 kV.

The thus obtained image has the color balance and density corresponding to the original image, and particularly it is excellent in three color separation, that is, it has no color stain.

While the invention has been described in detail and with reference to specific embodiment thereof, it will be apparent to one skilled in the art that various changes and modifications can be made therein without departing from the spirit and scope thereof.

What is claimed is:

1. A 2,6-di-tert-butyl-4-substituted thiopyrylium salt represented by Formula (I):

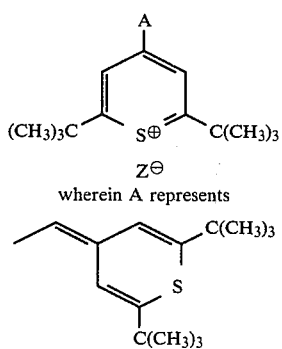

wherein A represents

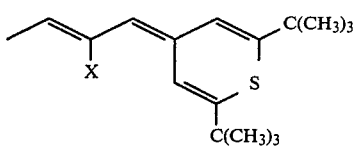

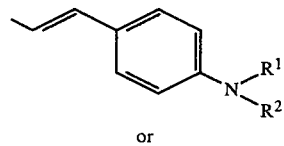

or

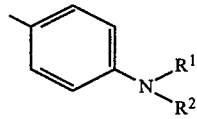

wherein $Z^\ominus$ is an anion, X is a hydrogen atom, an aryl group, a substituted aryl group or an alkyl group, and $R^1$ and $R^2$ are the same or different and represent alkyl groups.

2. 2,6-di-tert-butyl-4-(2,6-di-tert-butyl-4H-thiopyran-4-ylidenemethyl)thiopyrylium salt represented by formula I-(1):

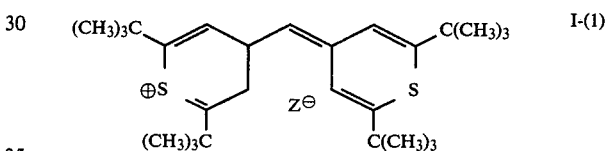

wherein $Z^\ominus$ is an anion.

3. 2,6-di-tert-butyl-4-[3-(2,6-di-tert-butyl-4H-thiopyran-4-ylidene)propene-1-yl]thiopyrylium salt or derivatives thereof represented by formula I-(2):

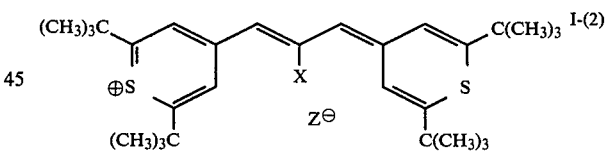

wherein $Z^\ominus$ is an anion, and X represents a hydrogen atom, an aryl group, a substituted aryl group or an alkyl group.

4. 2,6-di-tert-butyl-4-(4-disubstituted aminostyryl)thiopyrylium salt represented by formula I-(3):

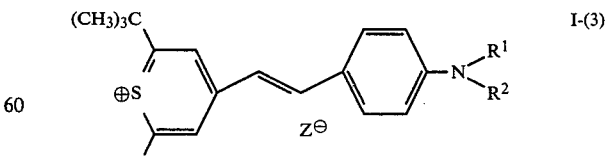

wherein $Z^\ominus$ is an anion, and $R^1$ and $R^2$ are the same or different and represent alkyl groups.

5. 2,6-di-tert-butyl-4-(4-disubstituted aminophenyl)-thiopyrylium salt represented by formula I-(4):

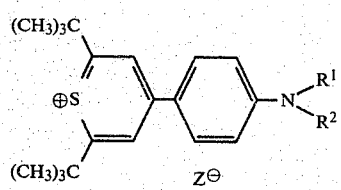

wherein $Z^\ominus$ is an anion, and $R^1$ and $R^2$ are the same or different and represent alkyl groups.

6. The thiopyrylium salt as claimed in claims 1, 2, 3, 4 or 5 wherein $Z^\ominus$ is an anion of a strong acid having a pKa of 5 or less.

7. The thiopyrylium salt as claimed in claim 1 wherein $Z^\ominus$ is a halogen anion selected from the group consisting of fluoride, chloride, bromide and iodide; an inorganic anion selected from the group consisting of perchlorate, periodate, tetrachloroaluminate, trichloroferrate (II), tetrafluoroborate, hexafluorophosphate, sulfate, hydrogensulfate and nitrate; or an organic anion selected from the group consisting of trifluoroacetate, trichloroacetate and p-toluenesulfonate.

8. A process for producing a 2,6-di-tert-butyl-4-(2,6-di-tert-butyl-4H-thiopyran-4-ylidenemethyl)thiopyrylium salt represented by formula I-(1):

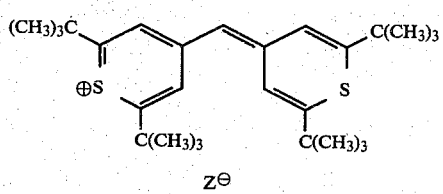

wherein $Z^\ominus$ is an anion which comprises reacting a 2,6-di-tert-butyl-4-methylthiopyrylium salt represented by formula (i)

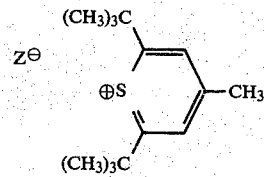

wherein $Z^\ominus$ is an anion;
and a 2,6-di-tert-butyl-4-(alkylthio)thiopyrylium salt represented by formula (ii)

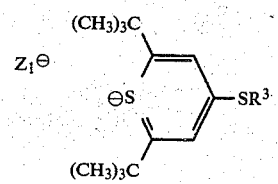

wherein $R^3$ is an alkyl group or a substituted alkyl group, and $Z_1^\ominus$ is a residue of an alkylating agent.

9. A process for producing a 2,6-di-tert-butyl-4-[3-(2,6-di-tert-butyl-4H-thiopyan-4-ylidene)propene-1-yl]thiopyrylium salt represented by formula I-(2):

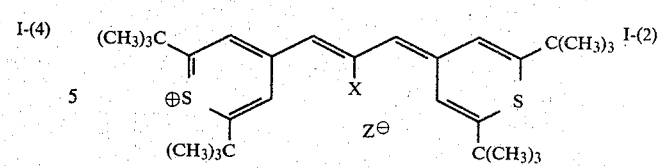

wherein $Z^\ominus$ is an anion and X is a hydrogen atom, an aryl group, a substituted aryl group or an alkyl group, which comprises reacting a 2,6-di-tert-butyl-4-methylthiopyrylium salt represented by formula (i):

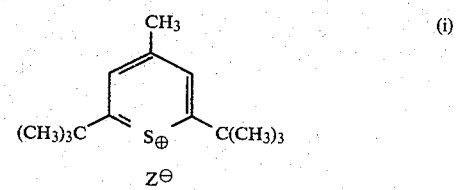

wherein $Z^\ominus$ is an anion and diphenylformamidine or the hydrochloride thereof, benzoyl chloride, p-substituted benzoyl chloride, or alkyl-N,N-diphenyl formamidine, the alkyl group having 1 to 4 carbon atoms.

10. A process for producing a 2,6-di-tert-butyl-4-[3-(2,6-di-tert-butyl-4H-thiopyran-4-ylidene)propene-1-yl]thiopyrylium salt represented by formula I-(2):

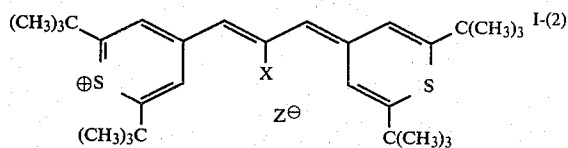

wherein Z is an anion and X is a hydrogen atom, which comprises reacting a 2,6-di-tert-butyl-4-methylthiopyrylium salt represented by formula (i):

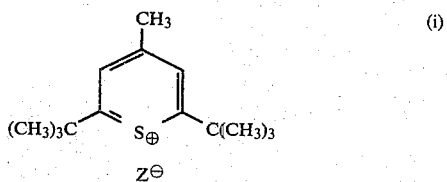

wherein $Z^\ominus$ is an anion and orthoformic acid ester.

11. A process for producing a 2,6-di-tert-butyl-4-(4-disubstituted aminostyryl)thiopyrylium salt represented by formula I-(3):

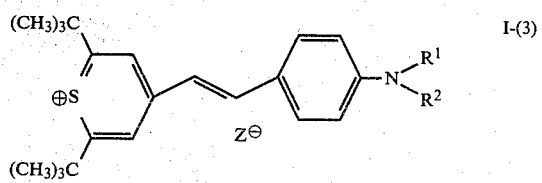

wherein $Z^\ominus$ is an anion and $R^1$ and $R^2$ are the same or different and represent alkyl groups, which comprises reacting a 2,6-di-tert-butyl-4-methylthiopyrylium salt represented by formula (i):

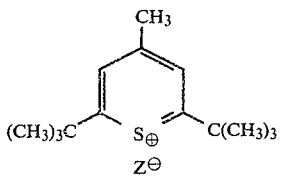

wherein Z⊖ is an anion, and 4-dialkylaminobenzaldehyde having 1 to 4 carbon atoms in the alkyl moiety in the presence of an amine or a carboxylic acid anhydride.

12. A process for producing a 2,6-di-tert-butyl-4-b [4-(disubstituted amino)phenyl]thiopyrylium salt represented by formula I-(4):

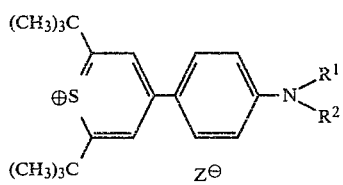

wherein Z⊖ is an anion and $R^1$ and $R^2$ are the same or different, and represent alkyl groups, which comprises reacting 2,6-di-tert-butyl-4H-thiopyran-4-one represented by formula (iii):

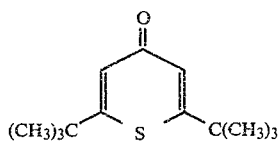

and an organometallic compound represented by formula (iv):

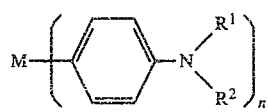

wherein M is a mono-, di- or tri-valent metal, a monohalogenated divalent metal or a dihalogenated trivalent metal, $R^1$ and $R^2$ are as defined above, and n is an integer of 1 to 3 and, thereafter, treating the reaction product with an acid.

13. The process as claimed in claim 8 wherein the reaction is carried out in a solvent.

14. The process as claimed in claims 8, 9, 10 or 11 wherein Z⊖ is an anion of a strong acid having a pKa of 5 or less.

15. The process as claimed in claim 8 wherein Z⊖ is at least one anion selected from the group consisting of halogen, methylsulfate, fluorosulfate and tetrafluoroborate.

16. The process as claimed in claim 8 wherein the reaction is carried out the reflux temperature of the solvent used.

17. The process as claimed in claim 8 wherein $R^3$ is a group selected from the group consisting of an unsubstituted alkyl group containing 1 to 6 carbon atoms, an alkyl group substituted with a phenyl group, a nitro- or halogenated phenyl group, an alkoxy group containing 1 to 5 carbon atoms, an amino group, an alkyl group and a sulfonic acid group.

18. The process as claimed in claim 8 wherein 1 mol of 2,6-di-tert-butyl-4-methylthiopyrylium salt represented by the formula (i) is reacted with 0.5 to 5 mols of 2,6-di-tert-butyl-4-(alkylthio)thiopyrylium salt represented by the formula (ii).

19. The process as claimed in claim 9 wherein the reaction is carried out in an organic solvent in the presence of an amine.

20. The process as claimed in claim 9 wherein the reaction is carried out in a carboxylic anhydride.

21. The process as claimed in claim 20 wherein sodium acetate or potassium acetate is added to the carboxylic anhydride.

22. The process as claimed in claim 9 wherein for the reaction, the 2,6-di-tert-butyl-4-methylthiopyrylium salt and the diphenylformamidine or hydrochloride thereof, are melted.

23. The process as claimed in claim 9 wherein 1 mol of the 2,6-di-tert-butyl-4-methylthiopyrylium salt is reacted with 0.2 to 5 mols of diphenylformamidine.

24. The process as claimed in claim 10 wherein at least one solvent selected from the group consisting of a carboxylic acid, a nitro compound, an amine, a nitrile, a ketone and a halogenated hydrocarbon is used.

25. The process as claimed in claim 11 wherein the reaction is carried out in a solvent in the presence of an amine.

26. The process as claimed in claim 11 wherein the reaction is carried out in 2 carboxylic anhydride.

27. The process as claimed in claim 25 wherein the amine is at least one amine selected from the group consisting of primary, secondary or tertiary alkylamines containing 1 to 25 carbon atoms; aromatic amines containing 6 to 25 carbon atoms; and nitrogen-containing heterocyclic compounds.

28. The process as claimed in claim 25 wherein the solvent is at least one member selected from the group consisting of alcohols, nitriles, ketones, nitro compounds and halogenated hydrocarbons.

29. The process as claimed in claim 12 wherein the acid is hydrofluoric acid, hydrochloric acid, hydrobromic acid, hydroiodic acid, perchloric acid, periodic acid, tetrafluoroboric acid, hexafluorophosphoric acid, sulfuric acid, nitric acid, trifluoroacetic acid or p-toluenesulfonic acid.

30. The process as claimed in claim 12 wherein the reaction is carried out in a solvent at a temperature of from −78° C. to the reflux temperature of the solvent.

31. The process as claimed in claim 12 wherein the amount of the organometallic compound represented by formula (iv) is 1 to 10 mols per mol of the 2,6-di-tert-butyl-4H-thiopyran-4-one represented by formula (iii).

32. The photoconductive composition comprising a photoconductor and, as a sensitizer a 2,6-di-tert-butyl-4-substituted thiopyrylium salt represented by formula (I):

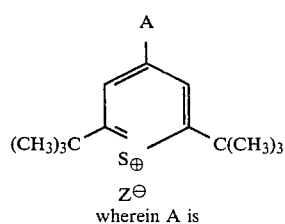

wherein A is

-continued

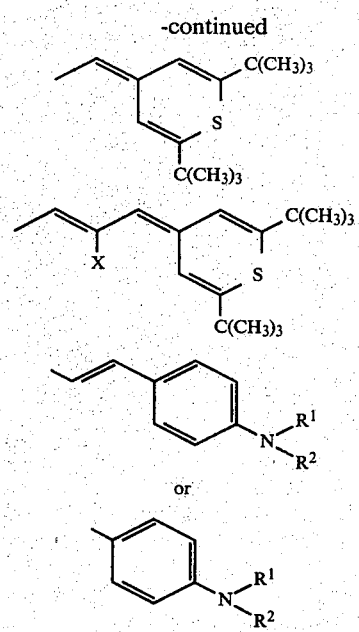

wherein $Z^\ominus$ is an anion, X is a hydrogen atom, an aryl group, a substituted aryl group or an alkyl group and $R^1$ and $R^2$ are the same or different and include an alkyl group.

33. The photoconductive composition comprising a photoconductor and, as a sensitizer a 2,6-di-tert-butyl-4-(2,6-di-tert-butyl-4H-thiopyran-4-ylidenemethyl)thiopyrylium salt represented by formula I-(1):

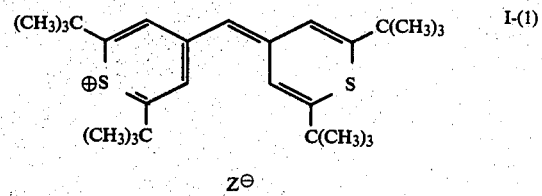

wherein $Z^\ominus$ is an anion.

34. The photoconductive composition comprising a photoconductor and as a sensitizer a 2,6-di-tert-butyl-4-[3-(2,6-di-tert-butyl-4H-thiopyran-4-ylidene)propene-1-yl] thiopyrylium salt or derivatives thereof represented by formula I-(2):

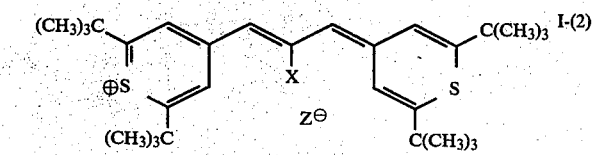

wherein $Z^\ominus$ is an anion and X represents a hydrogen atom, an aryl group, a substituted aryl group or an alkyl group.

35. The photoconductive composition comprising a photoconductor and as a sensitizer a 2,6-di-tert-butyl-4-(4-disubstituted aminostyryl)-thiopyrylium salt represented by formula I-(3):

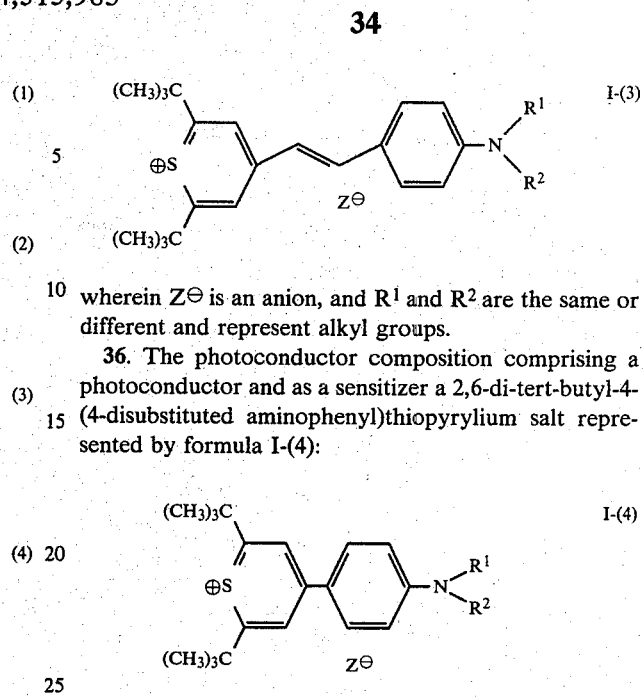

wherein $Z^\ominus$ is an anion, and $R^1$ and $R^2$ are the same or different and represent alkyl groups.

36. The photoconductor composition comprising a photoconductor and as a sensitizer a 2,6-di-tert-butyl-4-(4-disubstituted aminophenyl)thiopyrylium salt represented by formula I-(4):

wherein $Z^\ominus$ is an anion, and $R^1$ and $R^2$ are the same or different and represent alkyl groups.

37. The photoconductive composition of claims 32 to 36 wherein said photoconductor is selected from the group consisting of poly-N-vinyl carbazole, a triarylamine and a polyarylmethane.

38. The photoconductive composition of claims 32 to 36 wherein said sensitizer is present in an amount of about 0.0001 to 30 parts by weight per 100 parts by weight of photoconductor.

39. The photoconductive composition of claims 32 to 36 wherein said composition comprises particles of said photoconductor containing said sensitizer dispersed in an insulative liquid.

40. A light-sensitive material comprising an electrically conductive support having thereon a coating of a photoconductive composition comprising a photoconductor and, as a sensitizer a 2,6-di-tert-butyl-4-substituted thiopyrylium salt represented by the formula (I):

wherein

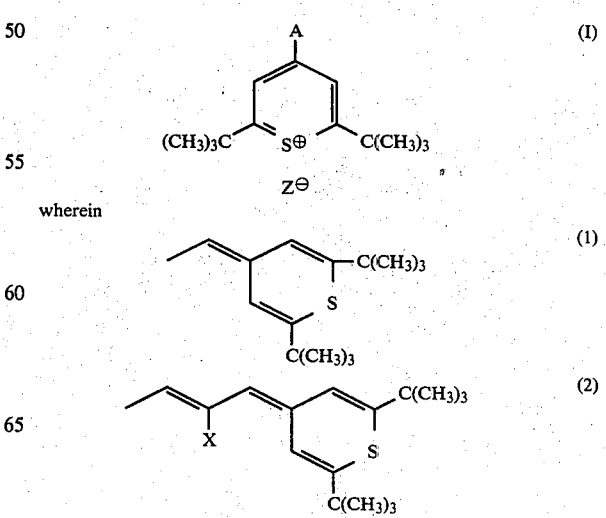

-continued

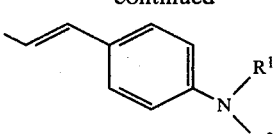
(3)

or

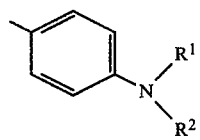
(4)

wherein $Z^\ominus$ is an anion, X is a hydrogen atom, an aryl group, a substituted aryl group or an alkyl group, and $R^1$ and $R^2$ are the same or different and include alkyl groups.

41. The light-sensitive material comprising an electrically conductive support having thereon a coating of a photoconductive composition comprising a photoconductor and as a sensitizer a 2,6-di-tert-butyl-4-(2,6-di-tert-butyl-4H-thiopyran-4-ylidenemethyl)thiopyrlium salt represented by the formula (I):

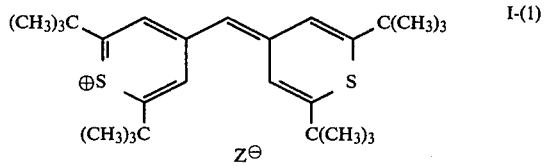
I-(1)

wherein $Z^\ominus$ is an anion.

42. The light-sensitive material comprising an electrically conductive support having thereon a coating of a photoconductive composition comprising a photoconductor and as a sensitizer a 2,6-di-tert-butyl-4-[3-(2,6-di-tert-butyl-4-H-thiopyran-4-ylidene)propene-1-yl]thiopyrylium salt or derivatives thereof:

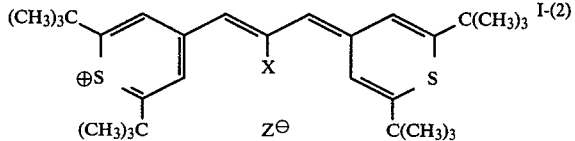
I-(2)

wherein $Z^\ominus$ is an anion, and X represents a hydrogen atom, an aryl group, a substituted aryl group or an alkyl group.

43. The light-sensitive material comprising an electrically conductive support having thereon a coating of a photoconductive composition comprising a photoconductor and, as a sensitizer a 2,6-di-tert-butyl-4-(4-disubstituted aminostyryl)thiopyrylium salt:

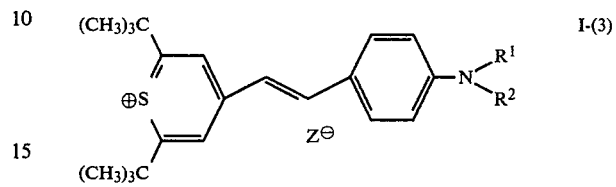
I-(3)

wherein $Z^\ominus$ is an anion, and $R^1$ and $R^2$ are the same or different and represent alkyl groups.

44. The light-sensitive material comprising an electrically conductive support having thereon a coating of a photoconductive composition comprising a photoconductor and, as a sensitizer a 2,6-di-tert-butyl-4-(4-disubstituted aminophenyl)thiopyrylium salt:

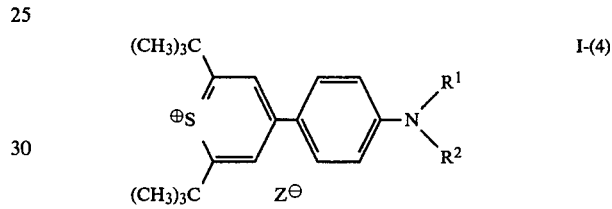
I-(4)

wherein $Z^\ominus$ is an anion, and $R^1$ and $R^2$ are the same or different and represent alkyl groups.

45. The light-sensitive material of claims 40 to 44 wherein said photoconductor is selected from the group consisting of a poly-N-vinyl carbazole, a triarylamine and a polyarylmethane.

46. The light-sensitive material of claims 40 to 44 wherein said sensitizer is present in an amount of about 0.0001 to 30 parts by weight per 100 parts by weight of sensitizer.

47. The light-sensitive material of claims 40 to 44 wherein said photoconductive composition comprises particles of said photoconductor containing said sensitizer dispersed in an insulative liquid.

* * * * *